United States Patent
Ateh et al.

(10) Patent No.: US 11,369,572 B2
(45) Date of Patent: Jun. 28, 2022

(54) FAS (APO-1,CD95) TARGETED PLATFORMS FOR INTRACELLULAR DRUG DELIVERY

(75) Inventors: Davidson Day Ateh, London (GB); Joanne Elizabeth Martin, Whitechapel London (GB)

(73) Assignee: Queen Mary & Westfield College, London (GB)

( * ) Notice: Subject to any disclaimer, the term of this patent is extended or adjusted under 35 U.S.C. 154(b) by 1133 days.

(21) Appl. No.: 13/386,349

(22) PCT Filed: Jul. 21, 2010

(86) PCT No.: PCT/GB2010/051207
§ 371 (c)(1),
(2), (4) Date: Mar. 30, 2012

(87) PCT Pub. No.: WO2011/010156
PCT Pub. Date: Jan. 27, 2011

(65) Prior Publication Data
US 2012/0177575 A1    Jul. 12, 2012

(30) Foreign Application Priority Data

Jul. 21, 2009  (GB) .................................. 0912645
Jun. 14, 2010  (GB) .................................. 1009891

(51) Int. Cl.
*A61K 9/16*      (2006.01)
*A61K 47/69*     (2017.01)
*A61K 9/19*      (2006.01)

(52) U.S. Cl.
CPC ........ *A61K 9/1647* (2013.01); *A61K 47/6921* (2017.08); *A61K 9/19* (2013.01)

(58) Field of Classification Search
CPC .... A61K 9/1647; A61K 47/6921; A61K 9/19; A61P 1/04; A61P 1/18; A61P 11/00; A61P 13/08; A61P 15/00; A61P 25/00; A61P 25/04; A61P 25/16; A61P 25/28; A61P 35/00
See application file for complete search history.

(56) References Cited

U.S. PATENT DOCUMENTS

| | | | |
|---|---|---|---|
| 2003/0022846 A1* | 1/2003 | Meredith et al. ............... | 514/37 |
| 2005/0003431 A1 | 1/2005 | Wucherpfennig et al. | |
| 2005/0084456 A1 | 4/2005 | Tang et al. | |
| 2006/0228420 A1 | 10/2006 | Martin | |

FOREIGN PATENT DOCUMENTS

| WO | WO 98/39354 | * 9/1998 |
|---|---|---|
| WO | WO 2006/097725 A2 | 9/2006 |
| WO | WO 2007/133807 A2 | 11/2007 |

OTHER PUBLICATIONS

Kim et al. BioMEMS and Biomedical Nanotechnology vol. I: Biological and Biomedical Nanotechnology Set: BioMEMS and Biomedical Nanotechnology Editor-in-chief: Ferrari, Mauro Lee, Abraham, Lee, James (Eds.), Chapter 2, 2006, 520 p.*
Desbarats et al. (Nature Medicine 4(12): 1377-1382, Dec. 1998).*
Shen et al. abstract from Transplantation 81(7): 1041-1048, Apr. 15, 2006.*
R&D Systems 2000 Catalog (p. 180, 2000).*
BD Pharmingen Technical Data Sheet, pp. 1 and 2. 2008.*
Weinberg et al. (American Pharmacists Association J. Pharm. Sci. 97:1681-1702, 2008).*
Ateh et al., The intracellular uptake of CD95 modified paclitaxel-loaded poly(lactic-co-glycolic acid) microparticles. Biomaterials. Nov. 2011;32(33):8538-47. doi: 10.1016/j.biomaterials.2011.07.060. Epub Aug. 6, 2011. With Supplementary Data.
International Search Report and Written Opinion for Application No. PCT/GB2010/051207 dated Nov. 23, 2010.
International Preliminary Report on Patentability for Application No. PCT/GB2010/051207 dated Feb. 2, 2012.
Lacronique et al., Bcl-2 protects from lethal hepatic apoptosis induced by an anti-Fas antibody in mice. Nat Med. Jan. 1996;2(1):80-6.
Mccarron et al., Antibody targeting of camptothecin-loaded PLGA nanoparticles to tumor cells. Bioconjug Chem. Aug. 2008;19(8):1561-9. Doi: 10.1021/bc800057g. Epub Jul. 16, 2008.
Micheau et al., Sensitization of Cancer Cells Treated With Cytotoxic Drugs to Fas-Mediated Cytotoxicity. J Natl Cancer Inst. Jun. 4, 1997;89(11):783-9.
Nagata, Apoptosis by death factor. Cell. Feb. 7, 1997;88(3):355-65.
Ogasawara et al., Lethal effect of the anti-Fas antibody in mice. Nature. Aug. 26, 1993;364(6440):806-9. Erratum in: Nature Oct. 7, 1993;365(6446):568.
Rensing-Ehl et al., Local Fas/APO-1 (CD95) ligand-mediated tumor cell killing in vivo. Eur J Immunol. Aug. 1995;25(8):2253-8.
Soezener et al., Targeted local activation of Fas in pancreatic beta-cells for treatment of insulinomas and disorders of pathological autonomic insulin secretion. Diabetologia. 2005;48:A189.

\* cited by examiner

*Primary Examiner* — Alana Harris Dent
(74) *Attorney, Agent, or Firm* — Wolf, Greenfield & Sacks, P.C.

(57) ABSTRACT

A delivery vehicle, for delivering a pharmaceutically active agent or a marker to a cell, comprising a ligand binding portion specific for a Fas Ligand, and a carrier for the pharmaceutically active agent or marker.

5 Claims, 25 Drawing Sheets

Figure 1A:
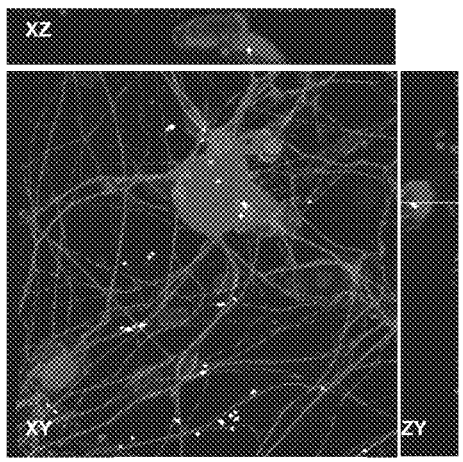
Figure 1B:
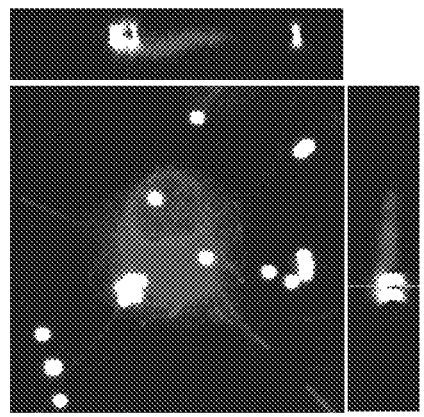
Figure 1C:
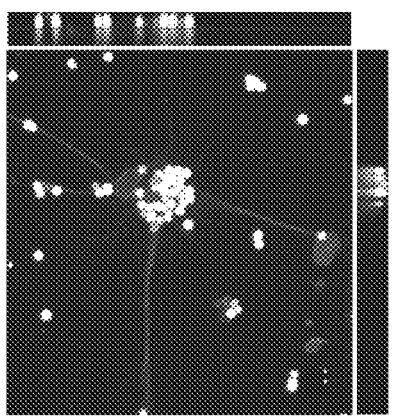
Figure 1D:
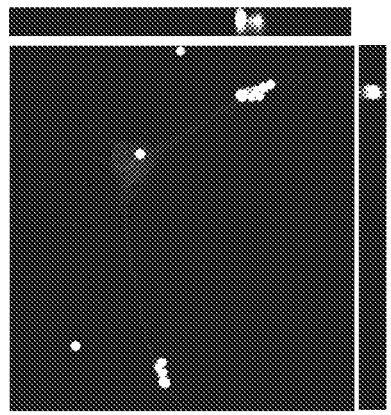

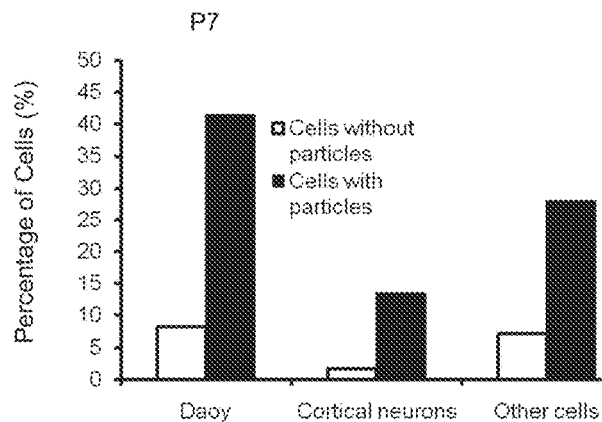
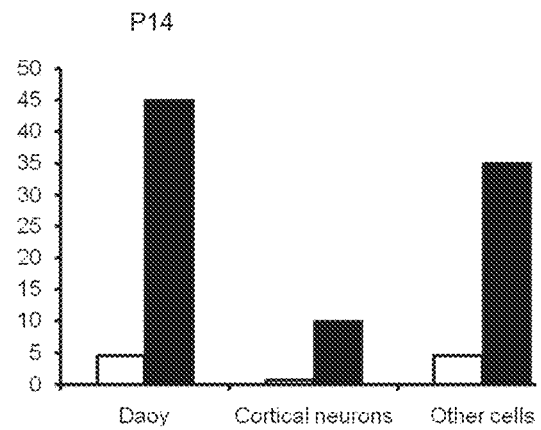
FIG. 14A
FIG. 14B
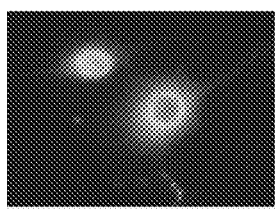
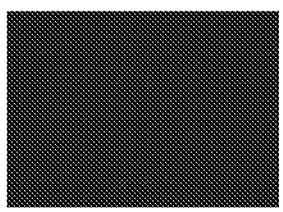
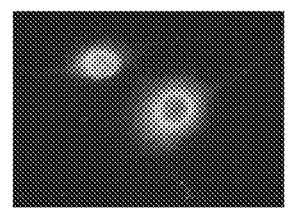
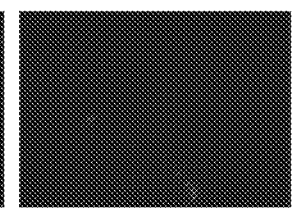
FIG. 15A
FIG. 15B
FIG. 15C
FIG. 15D
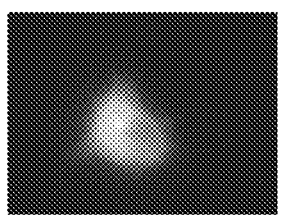
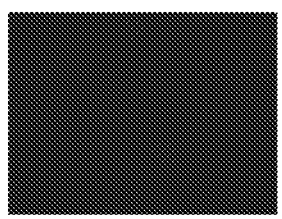
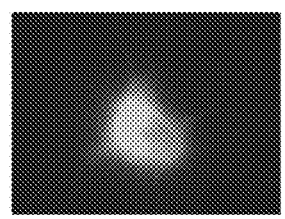
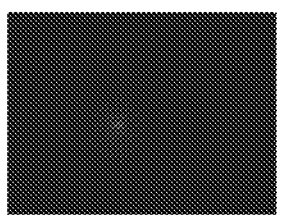
FIG. 15E
FIG. 15F
FIG. 15G
FIG. 15H

FAS (APO-1,CD95) TARGETED PLATFORMS FOR INTRACELLULAR DRUG DELIVERY

CROSS-REFERENCE TO RELATED APPLICATIONS

This application is a national stage filing under 35 U.S.C. § 371 of PCT International application PCT/GB2010/051207 designating the United States of America, filed Jul. 21, 2010, which claims priority to United Kingdom patent application numbers 0912645.9, filed Jul. 21, 2009, and 1009891.1, filed Jun. 14, 2010. Each of these applications is incorporated herein by reference in its entirety.

This invention relates to the field of drug delivery. More specifically, this invention relates to targeted delivery vehicles or drug carriers and to their use in therapeutic and diagnostic applications. Preferably, the vehicles or carriers in accordance with the invention have high specificity for their target cells and can provide effective intracellular delivery of pharmaceutically active agents or detectable markers. In an embodiment, the invention provides the means to deliver pharmaceutically active agents or detectable markers specifically to Fas Ligand-expressing cells. The invention extends to compositions and uses in therapy, particularly in the treatment or prophylaxis of neoplasm and neurological disorders.

Currently, most drugs are administered systemically. For most therapeutic agents, a large portion of the medication is eliminated from the body through systemic clearance, whilst only a small portion of the medication reaches the target organs or tissues. Moreover, systemic exposure of healthy tissues and organs to administered drugs can cause severe toxicity. The risk of toxicity can be exacerbated by the high dosages and large volumes of drug, which are often required to overcome poor bioavailability and to provide adequate distribution within a subject. On the contrary, targeted drug delivery seeks to concentrate the medication in the tissues or organs of interest while minimising systemic drug exposure. However, existing systems for targeted drug delivery are not ideal and current drug treatment strategies poorly address the toxicity problems associated with systemic drug exposure. This is especially so in the area of cancer therapy, where cytotoxic anti-cancer drugs can cause serious side effects as a result of the damage they can inflict upon healthy tissue. Therefore, an urgent need exists for targeted drug delivery strategies that will selectively deliver drugs to target tissues or organs. Such strategies should improve the efficacy of drug treatment by increasing the therapeutic indices of the drugs, while minimizing the risks of drug-related toxicity.

Furthermore, increased genomics, epigenomics and proteomics knowledge coupled with new therapeutic strategies such as RNA interference (Mello & Conte, 2004; Grimm, 2009) or peptide based intracellular modulators (Sawyer T K, 2009) are transforming the potential to treat diseases. In particular, it is desirable to formulate small molecules or larger biological drugs capable of acting on intracellular targets in order to selectively treat individual cell types or destroy aberrant cells as found in cancer, for example. However, intracellularly active drug candidates often fail to become pharmaceutically useful because they cannot penetrate the cell membrane to interact with their intracellular target molecules. Cell membranes are lipid bilayers, which typically act as semi-permeable barriers separating the inner cellular environment from the outer cellular (or external) environment. Current delivery systems for transporting drugs across the cell membrane are not as efficient and reliable as they might be. Therefore, there is a demand for an efficient intracellular drug delivery system.

According to a first aspect of the invention, there is provided a delivery vehicle, for delivering a pharmaceutically active agent or a marker to a cell, comprising a ligand binding portion specific for a Fas Ligand, and a carrier for the pharmaceutically active agent or marker.

The delivery vehicle can be a drug delivery vehicle comprising a ligand binding portion specific for a Fas Ligand and a carrier for the drug. The ligand binding portion can target a delivery vehicle in accordance with the invention to Fas Ligand-expressing cells. The delivery vehicle, thus, can provide intracellular delivery of a pharmaceutically active agent, marker or drug. The pharmaceutically active agent, marker or drug is preferably not an agent capable of specific binding to a Fas Ligand.

The carrier according to the invention can be a microparticle, nanoparticle, microcapsule, microsphere, micelle or liposome. Preferably, the carrier is a microparticle. The microparticle can have an average diameter of up to 0.01 µm, 0.05 µm, 0.1 µm, 0.2 µm, 0.5 µm, 1 µm, 2 µm, 5 µm or 10 µm. The microparticle can have an average diameter of between 0.1 µm and 10 µm, preferably between 0.2 µm and 5 µm, more preferably between 0.3 µm to 2 µm, even more preferably between 0.4 µm to 1.5 µm, and most preferably between 0.5 µm and 2 µm. The microparticle can comprise polylactic-co-glycolic acid (PLGA) matrix.

The ligand binding portion of the vehicle specific for a Fas Ligand can comprise a Fas receptor or a derivative thereof. It can also be a full-length Fas protein, or a fragment thereof. The ligand binding portion can comprise or consist of the extracellular domain of a Fas protein, or a fragment thereof, and preferably comprises or consists of a ligand binding domain of a Fas protein. The ligand binding portion of the vehicle can be a peptide, a protein, an aptamer, an antibody, an antibody fragment, a fusion protein or a chimeric protein. The ligand binding portion can be a Fas protein, or a fragment thereof, fused to a fragment crystallizable region (Fc region) of an immunoglobulin to form a chimeric fusion protein, i.e. Fas-Fc. Preferably, the immunoglobulin is a human immunoglobulin, such as IgG1. The vehicle can comprise a plurality of ligand binding portions specific for a Fas Ligand, and each of the latter can be embodied by any of the foregoing examples.

The, or each ligand binding portion can be of any origin, but it is preferably human or murine, or a combination thereof.

The, or each ligand binding portion can be coupled to the carrier, particularly when a microparticle, by surface absorption, adsorption, chemical conjugation or matrix incorporation, or covalently or non-covalently associated with the carrier, especially when the carrier is a microparticle. The, or each ligand binding portion can be coupled to the carrier via a linking molecule. The linking molecule can be a fragment crystallizable region (Fc) of an immunoglobulin, preferably a human immunoglobulin, such as IgG1.

Alternatively, linking systems such as avidin-biotin can be used to indirectly couple the ligand binding portion specific for a Fas Ligand to the carrier. Thus, the linking molecule can be avidin or biotin. The ligand binding portion specific for a Fas Ligand can be biotinylated and coupled to the avidin-coated carrier surface. Another linking molecule can be Staphylococcal protein A.

In preferred embodiments, the pharmaceutically active agent, marker or drug is attached to, or contained or encapsulated by the carrier, preferably for release at or within a target cell.

In a particularly preferred embodiment of the first aspect of the invention, the delivery vehicle is a microparticle containing a pharmaceutically active substance, wherein the microparticle is covalently or non-covalently associated with Fas, a derivative thereof, or a specific binding molecule for Fas Ligand.

The pharmaceutically active agent can be a protein, peptide, polypeptide, polynucleotide, polysaccharide, lipid, small molecule drug or any other biologically active substance. The pharmaceutically active agent can act intracellularly or can be specific for a component inside the target cell. The pharmaceutically active agent can be a cytotoxic or cytostatic agent. The pharmaceutically active agent can also include a cytotoxic radionuclide, chemical toxin or protein toxin. Preferably, the pharmaceutically active agent is an anti-cancer agent, especially doxorubicin or paclitaxel.

The marker can be a fluorescent marker, radionuclide or contrast agent. Hence, the marker can be a detectable marker or an imaging marker.

The pharmaceutically active agent, marker or drug can be contained or encapsulated by the carrier, particularly when the carrier is a microparticle. The active agent, marker or drug can be bound to or within the carrier or microparticle by chemical bonding or physically incorporated within the matrix of the material forming the carrier.

In a second aspect, the invention provides a delivery vehicle according to the first aspect of the invention for use in medicine, preferably for a therapeutic purpose. In this aspect, it is preferred that the pharmaceutically active agent, marker or drug is attached to, or contained or encapsulated by the carrier.

The therapeutic purpose can be the treatment of a disease or medical condition associated with neoplasm or a neurological disorder.

The invention also provides, in a further aspect, a method of treating a disease or medical condition, comprising administering to a subject a delivery vehicle in accordance with the first aspect of the invention, wherein the delivery vehicle includes an effective amount of the pharmaceutically active agent or drug.

The disease or condition can be a brain tumour, ovarian cancer, prostate cancer, breast cancer, an intraperitoneal tumour, an ovarian tumour, a gastrointestinal tumour, colon cancer, lung cancer, pancreatic cancer or a cancer type or tumour where the Fas Ligand is expressed in the tumour cells. Preferably, the disease or condition is ovarian cancer or medulloblastoma.

The disease or condition can be a neurological disease, including motor neuron disease, Alzheimer's disease, Parkinson's disease, neuropathic pain syndromes and peripheral nerve or spinal cord injuries.

According to a further aspect of the invention, there is provided a delivery vehicle according to the first aspect of the invention, for use in a diagnostic method comprising detecting Fas Ligand-expressing cells, wherein a marker is attached to, or contained or encapsulated by the carrier.

In another aspect, the invention provides a method of diagnosis comprising detecting Fas Ligand-expressing cells by administering to a subject a delivery vehicle according to the invention, wherein a marker is attached to, or contained or encapsulated by the carrier.

Preferably the diagnostic method, or method of diagnosis, is a method of diagnosing a neoplasm or neurological disorder.

The invention also provides pharmaceutical compositions comprising a delivery vehicle in accordance with the invention and one or more physiologically or pharmaceutically acceptable carrier, excipient, or stabilizer. Such compositions can be employed in any of the uses and methods described herein.

In another aspect, the invention provides a method for preparing a delivery vehicle in accordance with the invention, comprising the steps of forming a microparticle containing or encapsulating a pharmaceutically active agent, marker or drug and attaching a ligand binding portion specific for Fas Ligand to said microparticle.

The inventors have surprisingly found that the Fas/Fas Ligand system can enhance the uptake of microparticles. Using this approach, the inventors have shown that drugs can be delivered into target cells in microparticles coupled to Fas. This molecular targeting method enhances the intracellular uptake of microparticles by Fas Ligand-expressing cells.

In this patent application, the inventors describe for the first time, the novel use of Fas (also called Apo-1, CD95), fusion proteins of Fas (e.g. chimeric fusion protein: Fas fused to the fragment crystallizable region (Fc region) of an immunoglobulin (FasFc) etc . . . ), and/or equivalent moieties capable of replicating the role of Fas (e.g. peptides, proteins, aptamers etc . . . ) in the modification of drug delivery particles (e.g. polylactic-co-glycolic acid matrix (PLGA), polylactic acid (PLA), poly-ε-caprolactone (PCL), polydroxybutyrate (PHB) or chitosan biodegradable microspheres, silicon based particles, polyelectrolyte capsules, liposomes etc . . . ) to enhance their uptake and specificity to certain cells, including neurons, cancer cells and/or a range of Fas ligand (FasL, APO-1L, CD95L) expressing cells. From this invention, the inventors also describe the potential use of Fas (Apo-1, CD95), fusion proteins of Fas (e.g. FasFc etc . . . ), and/or equivalent moieties capable of replicating the role of Fas (e.g. peptides, proteins, aptamers etc . . . ) as drug conjugates for therapeutic delivery. Therefore, the invention enables the intracellular delivery of drugs and other substances to biological cells and is applicable in the biomedical research and therapeutics fields.

Whilst the Fas/Fas Ligand system has been extensively studied in apoptosis and various emerging roles in non-immune tissues, to the best of the inventors' knowledge, there is no prior art on the use of Fas (Apo-1, CD95) modified drug-loaded microparticles (e.g. PLGA, PCL, polyelectrolyte capsules or liposomes) or Fas (Apo-1, CD95) conjugated drugs to target and increase the intracellular uptake of drugs in cells. Furthermore, this invention is non-obvious and has considerable industrial applicability in the delivery of therapeutic formulations to patients suffering from cancer, neurological conditions and other diseases and/or as a research tool in biomedical sciences and drug development.

Intracellular drug delivery systems reduce unwanted side effects at distal sites and numerous technologies are under investigation including, for instance, targeted nanoparticles (Farokhzad et al., 2006; Gu et al., 2009; Faraji et al., 2009). It is also possible to use microparticles for intracellular drug delivery with the advantage of larger loading volumes for increased drug potency and sustained release.

However, there are limited studies investigating drug delivery using microparticles and they are essentially directed at professional phagocytes such as macrophages (Walter et al., 2001; Brandhonneur et al., 2009). The inventors and others have studied the phagocytic capacity of non-professional phagocytes, namely neurons, and demonstrated the ingestion of biological and synthetic particles above half a micron in diameter (Esselens et al., 2004; Bowen et al., 2007). Whilst this property was not widely recognised for neurons, it is well documented that many non-professional phagocytes are capable of ingesting relatively large particles including fibroblasts and epithelial cells (Rabinovitch, 1995). Improved understanding of the mechanisms that mediate phagocytosis in non-professional phagocytes could assist the design of drug delivery particles targeted at these cells. For example, it was recently shown that uptake can be modulated by specific cell surface receptors such as telencephalin in the case of hippocampal neurons (Esselens et al., 2004; patent pub no. WO/2006/030013 'The modulation of phagocytosis in neurons').

To the inventors' surprise, they found that Fas Ligand, which was previously not known to be involved in phagocytosis, enables intracellular uptake of Fas and Fas conjugates. In the present invention, the Fas (Apo-1, CD95) protein is used in an intracellular drug delivery system based on the modification of drug-loaded microparticles. The surface modification of drug loaded particles with Fas, fusion proteins of Fas and/or equivalent moieties capable of replicating the role of Fas significantly enhances the internalisation of microparticles by certain cells including neurons, cancer cells and/or a range of Fas ligand (FasL, APO-1L, CD95L) expressing cells.

The inventors have significant data (as illustrated in the Examples) showing that Fas (Apo-1, CD95) surface modified microparticles are preferentially ingested by a number of cell types compared to unmodified particles or those modified with other ligands. The inventors also show that biodegradable Fas (Apo-1, CD95) surface modified PLGA-based microparticles, developed into agent bearing microparticles, are taken up by cells and deliver the loaded agent inside studied cells. As illustrated in the Examples, the inventors have shown efficient intracellular uptake of microparticles including those of average diameter of about 0.5-1.5 μm via Fas/Fas Ligand-assisted phagocytosis. Furthermore, the Examples show functional effects when biological cells take up microparticles loaded with anti-cancer drugs. Hence, the data set out in the Examples illustrates the novelty, inventiveness and usefulness of the therapeutic platform based on the use of Fas (Apo-1, CD95).

Therefore, delivery vehicles in accordance with the invention can be used to significantly reduce the total amount of drug administered whilst increasing the drug concentration at its target site. They, thus, can be used to improve the function of cytotoxics and other drugs in a wide range of diseases, such as neoplasm and neurological disorders, potentially increasing drug efficacy whilst reducing toxicity. They can also provide a delivery option for promising therapeutics not currently considered viable for development. Embodiments of the invention in which the pharmaceutically active agent or drug is encapsulated by the carrier or microparticle are particularly effective in this regard, because they reduce the amount of the agent or drug that can become biologically available until it had reached its target.

As will be known to a person skilled in the art, Fas (also known as Apo-1, CD95) is a member of the TNF/NGF receptor superfamily and is expressed as a cell membrane receptor or in a soluble form. The full sequence and transcripts for the human Fas (Apo-1, CD95) gene are described on the Ensembl database for *Homo sapiens* and some other living species (www.ensembl.org/Homo_sapiens/Gene/Summary?g=ENSG00000026103). The full length sequence and transcripts for the murine Fas gene are described on the Ensembl database for mouse genome (*Mus musculus*) (www.ensembl.org/Mus_musculus/Gene/Summary?db=core:g=ENSMUSG00000024778) and are described in Watanabe-Fukunaga et al., 1992. Fas mediates the induction of apoptosis in selected cells through binding with its ligand Fas Ligand (FasL), also known as Apo-1L and CD95L. Fas Ligand is a TNF superfamily member and induces programmed cell death upon binding with Fas in selected cells. The Fas/Fas Ligand system has been mostly studied in relation to apoptosis (Nagata, 1997) and disregulation of the Fas/Fas Ligand system is associated with a breakdown in immune homeostasis (Nagata and Suda, 1995; Lettau et al., 2008). However, beyond a singular role in immune system tissues, there are reports suggesting functions for the Fas/Fas Ligand system in various tissues such as the central nervous system, where Fas and Fas Ligand are expressed by non-immune cells (Choi and Benveniste, 2004). This includes novel roles in Parkinson's (Landau et al., 2005) and Alzheimer's (Ethell et al., 2002) diseases, control of branching in neurons (Zuliani et al., 2006) and neuroprotection in spinal cord injury (Ackery et al., 2006) for instance.

Furthermore, there is a strong case that the expression of Fas Ligand in cells of certain tissues or organs including the central nervous system (Choi and Benveniste, 2004), the eye (Ferguson and Griffith, 2006) and tumours (O'Connell et al., 2001; Ryan et al., 2005) confers immune privileged status on these tissues or organs by enabling the killing of activated Fas-positive immunocytes (Flügel et al., 2000; Green and Ferguson, 2001). Tumour cells expressing Fas Ligand include human lung carcinomas shown to be capable of killing T-cells in co-culture experiments (Niehans et al., 1997); this ability was inhibited if the fusion protein FasFc was added to cultures. They also include brain tumours such as glioblastoma and medulloblastoma (Gratas et al., 1997, Weller et al., 1998), colon cancer (O'Connell et al., 1998) where downregulation of Fas Ligand by in vivo transfection resulted in reduced tumour sizes due to an increase in the number of tumour infiltrating lymphocytes (Ryan et al., 2005) and ovarian cancer (Abrahams et al. 2003) where the induction of Fas Ligand increased apoptosis in T-lymphocytes (Meng et al., 2004).

The carrier or microparticle can comprises a polymer selected from the group consisting of polyalkylenes, polycarbonates, poly(dioxanones), polyanhydrides, polyhydroxyacids, polyfumarates, polycaprolactones, polyamides, polyacetals, polyethers, polyesters, poly(orthoesters), polyhydroxybutyrates, polyvinyl alcohols, polyurethanes, polyphosphazenes, polyacrylates, polymethacrylates, polycyanoacrylates, polyureas, polystyrenes, polyamines, poly(arylates), polycarbonates, poly(propylene fumarates), polyhydroxyalkanoates, polyketals, polyesteramides, polyhydroxyvalyrates, polyorthocarbonates, poly(vinyl pyrrolidone), polyalkylene oxalates, polyalkylene succinates, poly(malic acid), poly(methyl vinyl ether) and poly(maleic anhydride).

The carrier or microparticle can comprise PLGA (poly-lactic-co-glycolic acid) matrix, PLA (polylactic acid), PCL (poly-ε-caprolactone) or PHB (Polyhydroxybutyrate) or is a chitosan biodegradable microsphere, a silicon or silicon-based particle, a polyelectrolyte capsule, a dendrimer or a liposome. The carrier or microparticle can be non-polymeric. Preferably, the microparticles comprise PLGA matrix.

Biodegradability of a microparticle in accordance with the invention can be determined or examined through incubation with any suitable medium in vitro. Biodegradability can also be examined through parenteral injection of the microparticles, for example subcutaneously or intramuscularly, and histological examination of the tissue as a function of time. The biodegradable microparticle, after parenteral administration, can be dissolved in the body to form endogenic substances, ultimately, for example, lactic acid.

Biocompatibility of a microparticle in accordance with the invention can be examined through parenteral administration of the microparticles, for instance subcutaneously or intramuscularly, and histological evaluation of the tissue. Most studies relating to microparticles have considered drugs formulated within a polylactic-co-glycolic acid (PLGA) matrix. PLGA is a biodegradable polymer approved by regulators including the US FDA (Food and Drug Administration) for clinical use and is commonly used in orthopaedic implants and systemic drug delivery depot systems (e.g. Trelstar®, Lupron Depot®, Risperdal Consta®). Drug loading into PLGA microparticles, including bioactive proteins (Giteau et al., 2008) and nucleic acids (Patil and Panyam, 2009), is typically carried out during synthesis. Furthermore, PLGA drug carriers can be surface functionalised with suitable ligands so as to increase their target specificity either through simple adsorption or chemical conjugation. Farokhzad and colleagues (2006) exemplified such an approach using aptamers functionalised to docetaxel-loaded PEGylated PLGA nanoparticles in order to target prostate cancer cells. It is also possible to entrap drugs for intracellular delivery within other types of biodegradable microparticles including poly-ε-caprolactone (Sinha et al., 2004) and a wide variety of systems such as polyelectrolyte microcapsules (Sukhorukov et al., 2007; Muñoz Javier et al., 2008) or liposomes (Huwyler et al., 2008).

The pharmaceutically active agent can be an antitumour agent, antibiotic, anti-inflammatory agent, antihistamine, sedative, muscle-relaxant, antiepileptic agent, antidepressant, antiallergic agent, bronchodilator, cardiotonic agent, antiarrhythmic agent, vasodilator, antidiabetic, anticoagulant, haemostatic agent, narcotic and steroid.

The pharmaceutically active agent can be a cytotoxic, cytostatic or other drug. The cytotoxics, cytostatics or drugs can be of platin (derivative) and taxol classes. The cytostatics or drugs can be selected from the group consisting of, for example, cisplatin, satraplatin, oxaliplatin, carboplatin, nedaplatin, chlorambucil, cyclophosphamid, mephalan, azathioprin, fluorouracil, mercaptopurin, methrexat, nandrolon, aminogluthemid, medroxyprogesterone megestrolacetate, procarbazin, docetaxel, paclitaxel, epipodophyllotoxin, podophyllotoxin, vincristine, docetaxel, daunomycin, doxorubicin, mitoxantrone, topotecan, bleomycin, gemcitabine, fludarabine, and 5-FUDR. Preferably, the biological active agent is an anti-cancer agent, especially doxorubicin or paclitaxel.

The cytotoxic nuclide or radiotherapeutic isotope can be an alpha-emitting isotope such as $^{225}$Ac, $^{211}$At, $^{212}$Bi, $^{213}$Bi, $^{212}$Pb, $^{224}$Ra or $^{223}$Ra. Alternatively, the cytotoxic radionuclide can be a beta-emitting isotope such as $^{186}$Rh, $^{188}$Rh, $^{177}$Lu, $^{90}$Y, $^{131}$I, $^{67}$Cu, $^{64}$Cu, $^{153}$Sm or $^{166}$Ho. Alternatively, cytotoxic radionuclide can emit Auger and low energy electrons and include the isotopes $^{125}$I, $^{123}$I or $^{77}$Br.

Suitable detectable or imaging markers include, but are not limited to, fluorescent molecules such as those described by Molecular Probes (Handbook of fluorescent probes and research products), such as Rhodamine, fluorescein (such as fluorescein isothiocyanate (FTIC)), Texas red, Acridine Orange, Alexa Fluor (various), Allophycocyanin, 7-amino-actinomycin D, BOBO-I, BODIPY (various), Calcien, Calcium Crimson, Calcium green, Calcium Orange, 6-carboxyrhodamine 6G, Cascade blue, Cascade yellow, DAPI, DiA, DiD, DiI, DiO, DiR, ELF 97, Eosin, ER Tracker Blue-White, EthD-1, Ethidium bromide, Fluo-3, Fluo4, FM1-43>FM4-64, Fura-2, Fura Red, Hoechst 33258, Hoechst 33342, 7-hydroxy-4-methylcoumarin, Indo-1, JC-I, JC-9, JOE dye, Lissamine rhodamine B, Lucifer Yellow CH, LysoSensor Blue DND-167, LysoSensor Green, LysoSensor Yellow/Blu, Lysotracker Green FM, Magnesium Green, Marina Blue, Mitotracker Green FM, MitoTracker Orange CMTMRos, MitoTracker Red CMXRos, Monobromobimane, NBD amines, NeruoTrace 500/525 green, Nile red, Oregon Green, Pacific Blue. POP-I, Propidium iodide, Rhodamine 110, Rhodamine Red, R-Phycoerythrm, Resorfm, RH414, Rhod-2, Rhodamine Green, Rhodamine 123, ROX dye, Sodium Green, SYTO blue (various), SYTO green (Various), SYTO orange (various), SYTOX blue, SYTOX green, SYTOX orange, Tetramethylrhodamine B, TOT-I, TOT-3, X-rhod-1, YOYO-1, or YOYO-3.

Additionally radionuclides can be used as imaging agents. Suitable radionuclides can include radioactive species of Fe(III), Fe(II), Cu(II), Mg(II), Ca(II), and Zn(II) Indium, Gallium and Technetium. Other suitable contrast agents can include metal ions generally used for chelation in paramagnetic T1-weighted or T2-weighted MRI contrast agents, and include di- and tri-valent cations such as copper, chromium, iron, gadolinium, manganese, erbium, europium, dysprosium and holmium. Metal ions that can be chelated and used for radionuclide imaging can include metals such as gallium, germanium, cobalt, calcium, indium, indium, rubidium, yttrium, ruthenium, yttrium, technetium, rhenium, platinum, thallium and samarium. Additionally metal ions known to be useful in neutron-capture radiation therapy include boron and other metals with large nuclear cross-sections. Also suitable can be metal ions useful in ultrasound contrast, and X-ray contrast compositions. Examples of other suitable contrast agents can include gases or gas emitting compounds, which are radioopaque.

The Fas Ligand-expressing cells can be detected using standard imaging or detection techniques known to a person skilled in the art. For example, microscopy, flow cytometry, medical ultrasonography, radiography (such as projection radiography and fluoroscopy), nuclear medicine imaging (such as scintillation cameras), magnetic resonance imaging (MRI), photoacoustic imaging, digital infrared imaging thermography or tomography.

Many microencapsulation techniques exist which can produce a variety of particle types and sizes under various conditions. Methods typically involve solidifying emulsified liquid polymer droplets by changing temperature, evaporating solvent, or adding chemical cross-linking agents.

If the microencapsulation process does not produce particles having a homogenous size range, then the particles can be separated using standard techniques such as sieving or filtering to produce a population of particles having the desired size range. All particles are characterised in terms of particle size distribution by standard techniques, such as optical microscopy, Coulter Multisizer (Beckman Coulter, dynamic light scattering (Malvern Zetasizer), transmission electron microscopy (TEM), scanning electron microscopy (SEM), and quasi-elastic light scattering (QELS). The microparticle of the invention can be of average diameter of up to 0.01 μm, 0.05 μm, 0.1 μm, 0.2 μm, 0.5 μm, 1 μm, 2 μm, 5 μm or 10 μm.

Common microencapsulation techniques include interfacial polycondensation, spray drying, hot melt microencapsulation, and phase separation techniques (solvent removal and solvent evaporation). Such techniques are described in US2001020011, Mathiowitz and Langer 1987; Mathiowitz, et al., 1987, 1988, 1990, 1992; Benita, et al., 1984.

Interfacial polycondensation can be used to microencapsulate a core material (such as the pharmaceutically active agent or marker of the invention) in the following manner. One monomer and the core material are dissolved in a solvent. A second monomer is dissolved in a second solvent (typically aqueous) which is immiscible with the first. An emulsion is formed by suspending the first solution through stirring in the second solution. Once the emulsion is stabilized, an initiator is added to the aqueous phase causing interfacial polymerization at the interface of each droplet of emulsion.

Spray drying is typically a process for preparing 1-10 micron sized microspheres in which the core material to be contained or encapsulated (such as the pharmaceutically active agent or marker of the invention) is dispersed or dissolved in a polymer solution (typically aqueous), the solution or dispersion is pumped through a micronizing nozzle driven by a flow of compressed gas, and the resulting aerosol is suspended in a heated cyclone of air, allowing the solvent to evaporate from the microdroplets. The solidified particles pass into a second chamber and are trapped in a collection flask.

Hot melt microencapsulation is a method in which a core material (such as the pharmaceutically active agent or marker of the invention) is added to molten polymer. This mixture is suspended as molten droplets in a non-solvent for the polymer (often oil-based) which has been heated to 10° C. above the melting point of the polymer. The emulsion is maintained through vigorous stirring while the non-solvent bath is quickly cooled below the glass transition of the polymer, causing the molten droplets to solidify and entrap the core material. Microspheres produced by this technique typically range in size from 50 microns to 2 mm in diameter.

In solvent evaporation microencapsulation, the polymer is typically dissolved in a water immiscible organic solvent and the material to be contained or encapsulated (such as the pharmaceutically active agent or marker of the invention) is added to the polymer solution as a suspension or solution in organic solvent. An emulsion is formed by adding this suspension or solution to a beaker of vigorously stirring water (often containing a surface active agent to stabilize the emulsion). The organic solvent is evaporated while continuing to stir. Evaporation results in precipitation of the polymer, forming solid microcapsules containing core material.

An alternative solvent evaporation process involves using microsieves. The polymer is typically dissolved in a water immiscible organic solvent and the material to be contained or encapsulated (such as the pharmaceutically active agent or marker of the invention) is added to the polymer solution as a suspension or solution in organic solvent, such as dichloromethane. Next, this suspension or solution is filtered through a PTFE filter. Thereafter the polymer is emulsified through a microsieve membrane (such as Nanomi BV, The Netherlands), which is a microfabricated membrane with uniform pores along the surface, into an aqueous solution containing an emulsifier. The resultant emulsion is left to stir at room temperature for at least three hours to evaporate the solvent. The hardened microspheres is concentrated by filtration and washed repeatedly. Subsequently, the particles were freeze-dried and stored at low temperation (e.g. at −20° C.) until evaluation.

In solvent removal microencapsulation, the polymer is typically dissolved in an oil miscible organic solvent, and the material to be contained or encapsulated (such as the pharmaceutically active agent or marker of the invention) is added to the polymer solution as a suspension or solution in organic solvent. An emulsion is formed by adding this suspension or solution to a beaker of vigorously stirring oil, in which the oil is a non-solvent for the polymer and the polymer/solvent solution is immiscible in the oil. The organic solvent is removed by diffusion into the oil phase while continuing to stir. Solvent removal results in precipitation of the polymer, forming solid microcapsules containing core material.

The pharmaceutically active agent or a marker can comprise about 25% w/w, or more, of the vehicle or microparticle. Preferably, the pharmaceutically active agent or marker comprises up to 0.01%, 0.1%, 1%, 5%, 10%, 15% 20%, 25%, 30% or 40% (w/w) of the vehicle or microparticle.

The microparticle can have an average diameter of about 0.5-1.5 µm, and can be produced by any of the processes described above.

The ligand binding portion specific for Fas Ligand, for example, the Fas protein, a derivative thereof, or a chimeric protein thereof, is preferably adsorbed or chemically conjugated to the surface of the carrier or microparticle. It can also be incorporated in the matrix of the carrier or microparticles. It is appreciated by those skilled in the art that this step can be performed by standard techniques, such as simple adsorption, chemical conjugation techniques, or incorporation into the matrix of the microparticles. The ligand binding portion specific for a Fas Ligand is preferably attached to or associated with the surface of the carrier (such as a microparticle). The binding portion can comprise up to about 0.01%, 0.1%, 1%, 5%, 10%, 15% 20%, 25% or 30% w/w of the vehicle or microparticle.

Thus, the invention provides a method for the preparation of a microparticle containing a pharmaceutically active substance, wherein the microparticle is covalently or non-covalently associated with Fas, a derivative thereof, or a specific binding molecule for Fas Ligand comprising associating the microparticle with Fas, a derivative thereof, or a specific binding molecule for Fas Ligand by surface absorption, adsorption, chemical conjugation or by matrix incorporation.

Suitable pharmaceutically acceptable carriers, excipients, or stabilizers are preferably non-toxic and do not interfere with the effectiveness or the biological activity of the active ingredients. The pharmaceutically-acceptable carrier can be one or more compatible solid or liquid fillers, diluents or encapsulating substances which are suitable for administration to a human or other vertebrate animal. The pharmaceutically-acceptable carrier can be an organic or inorganic ingredient, natural or synthetic, with which the active ingredient is combined to facilitate the application.

Pharmaceutical compositions can be formulated in a conventional manner using one or more physiologically acceptable carriers including excipients and auxiliaries which facilitate processing of the active compounds into preparations which can be used pharmaceutically. Proper formulation is dependent upon the route of administration chosen. Typical formulations for injection include a carrier such as sterile saline or a phosphate buffered saline. Viscosity modifying agents and preservatives are also frequently added. Suitable pharmaceutically acceptable excipients include, but are not limited to, diluents, binders, lubricants, disintegrants, colorants, stabilizers, and surfactants.

It will be appreciated that the delivery vehicle or the composition of the invention can be used as an adjunct to, or in combination with, known therapies for treating, ameliorating, or preventing neoplasm or neurological disorders. The delivery vehicle or the composition according to the invention can be combined in compositions having a number of different forms depending, in particular, on the manner in which the composition is to be used.

Fas Ligand-expressing cells can be found in brain tumours, ovarian cancer, prostate cancer, breast cancer, intraperitoneal tumours, ovarian tumours, gastrointestinal tumours, colon cancer, lung cancer, pancreatic cancer and cancer types. Fas Ligand-expressing cells can also be found in cells associated with neurological diseases, motor neuron disease, Alzheimer's disease, Parkinson's disease, neuropathic pain syndromes and peripheral nerve and spinal cord injuries.

A subject can be a vertebrate, mammal, or domestic animal. Hence, the delivery vehicle or composition according to the invention can be used to treat any mammal, for example livestock (e.g. a horse), pets, or can be used in other veterinary applications. Most preferably, the subject is a human being.

An effective amount of the delivery vehicle or the composition of the invention can be an amount which allows an effective amount of the pharmaceutically active agent to reach the target and thereby producing a therapeutic effect in the subject. The actual effective amount of the delivery vehicle or composition comprising pharmaceutically active agents can vary according to factors including the specific agent, substance or combination thereof being utilised, the density and/or nature of the ligand binding portion specific for Fas Ligand, the release characteristics of the encapsulated pharmaceutically active agents, the particular composition formulated, the mode of administration, and the age, weight, condition of the subject being treated, as well as the route of administration and the disease or disorder.

The delivery vehicle or composition according to the invention can be suitable for parenteral administration. Parenteral administration can be subcutaneous, intravenous, intramuscular, intra-articular, intra-synovial, intraperitoneally, intrasternal, intrathecal, intrahepatic, intralesional, intratumoural and intracranial injection or infusion techniques. If administered parentally, the pharmaceutical compositions are administered preferably subcutaneously or intravenously.

Nonetheless, administration of the delivery vehicle or the composition according to the invention can be accomplished by any acceptable method which allows an efficient amount of the delivery vehicle or the composition to reach their target. The particular mode selected will depend upon factors such as the particular formulation, the severity of the state of the subject being treated, and the dosage required to induce an effective treatment.

All of the features described herein (including any accompanying claims, abstract and drawings), and/or all of the steps of any method or process so disclosed, can be combined with any of the above aspects in any combination, except combinations where at least some of such features and/or steps are mutually exclusive. For a better understanding of the invention and to show how embodiments of the same can be carried into effect, reference will now be made, by way of example, to the accompanying drawings, in which:

FIGS. 1A-1D show uptake of unmodified synthetic particles in primary sensory neurons. Confocal microscopy shows the intracellular uptake of synthetic particles (round microspheres) in β3 tubulin labelled dorsal root ganglion neurons (nuclei are seen in the centre of cells). (FIGS. 1A, 1B) 1 μm polystyrene microspheres. (FIGS. 1C, 1D) 2 μm polyelectrolyte capsules loaded with fluorochrome (FITC) conjugated bovine serum albumin. Particles were seen in both the cell body and neuritis.

Figure 2A:
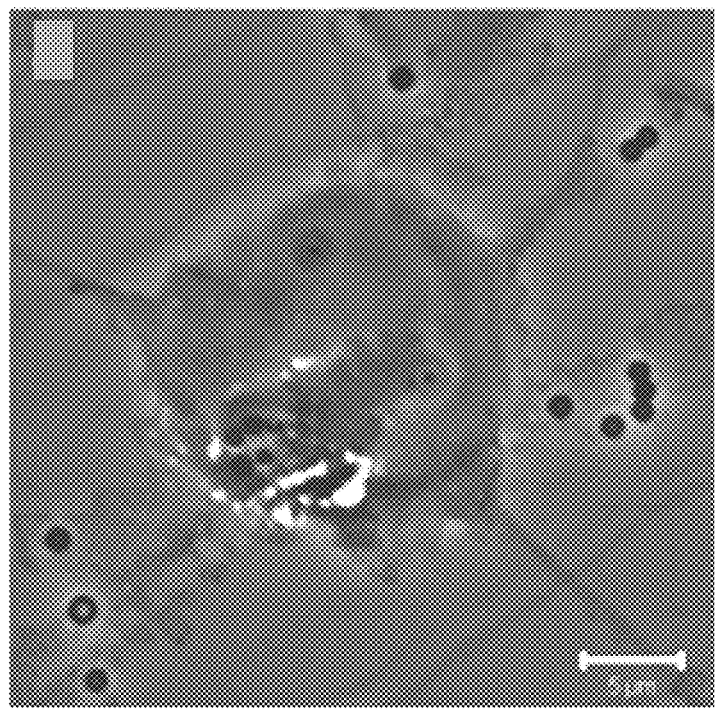
Figure 2B:
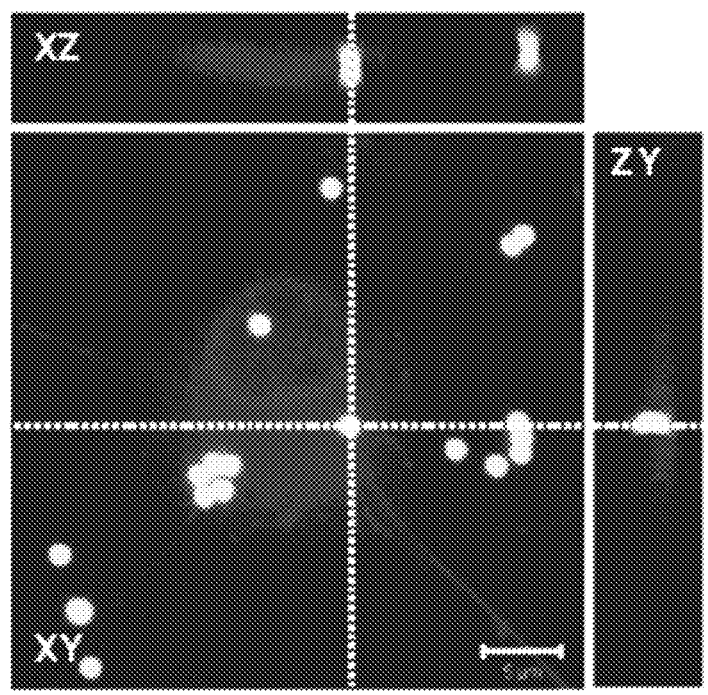
Figure 2C:
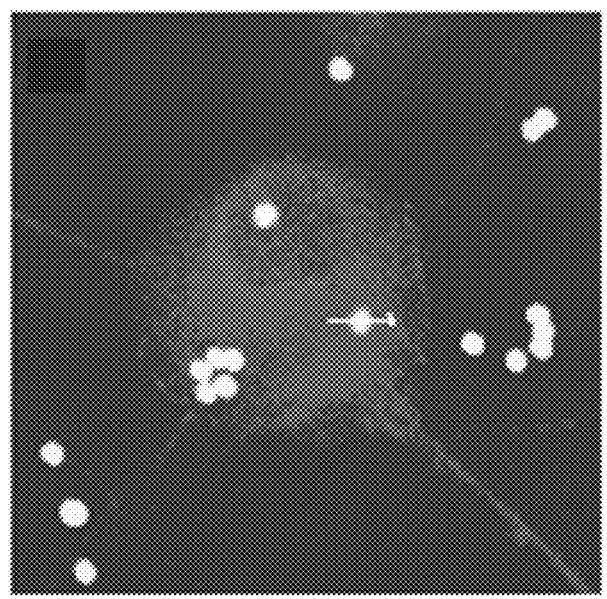
Figure 2D:
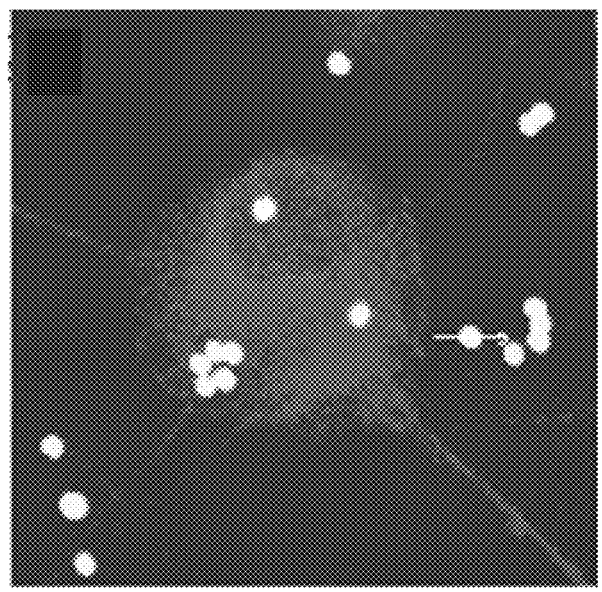
Figure 2E:
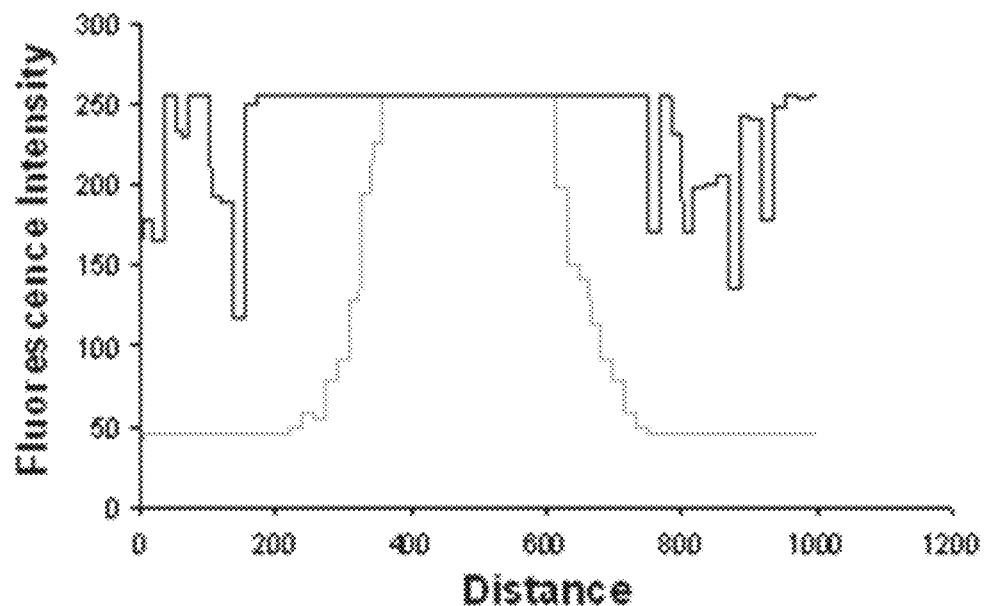
Figure 2F:
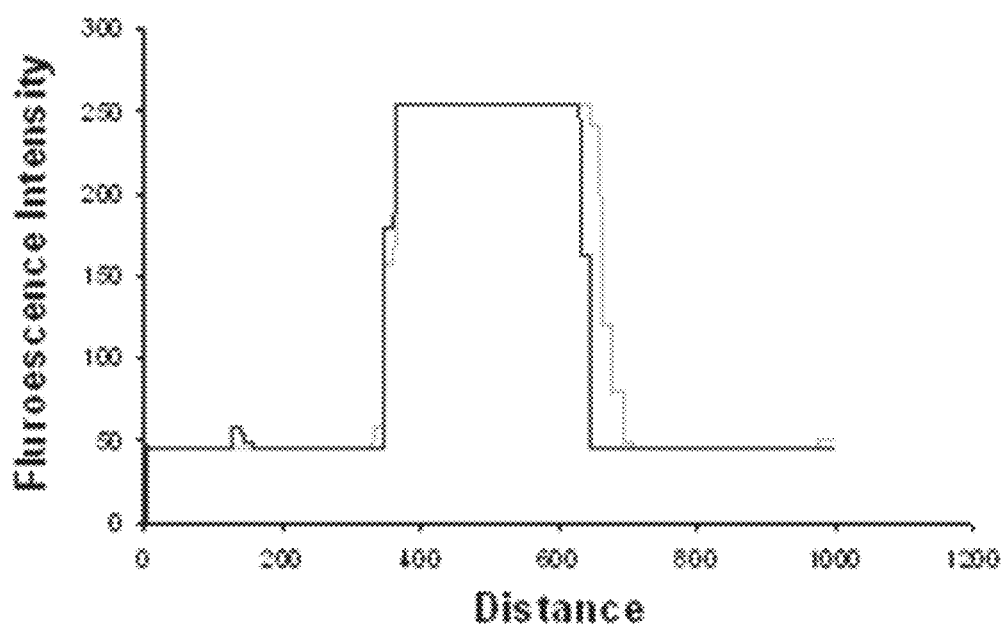

FIGS. 2A-2E show uptake of unmodified synthetic particles in primary sensory neurons. Confocal microscopy of dorsal root ganglia neurons (taken from Bowen et al., 2007). (FIG. 2A) Bright field image. (FIG. 2B) Confocal microscopy of rat dorsal root ganglia neurons stained with an antibody against β3-tubulin, after incubation with 1 μm microspheres (round microspheres). From the top and side panels showing z-stack cross-sections along the dotted white line in the XY plane it can be seen that the microsphere is internalised. (FIGS. 2C, 2E) Fluorescence intensity profile of the green and red channels inside the neuron (FIG. 2E) highlighted by the white line (FIG. 2C) shows co-localisation of the microsphere and β3-tubulin labelling within a 0.33 μm optical slice. (FIGS. 2D, 2F) Fluorescence intensity profile of the green and red channels outside the neuron (FIG. 2F) highlighted by the white line (FIG. 2D) shows no co-localisation.

Figure 3A:
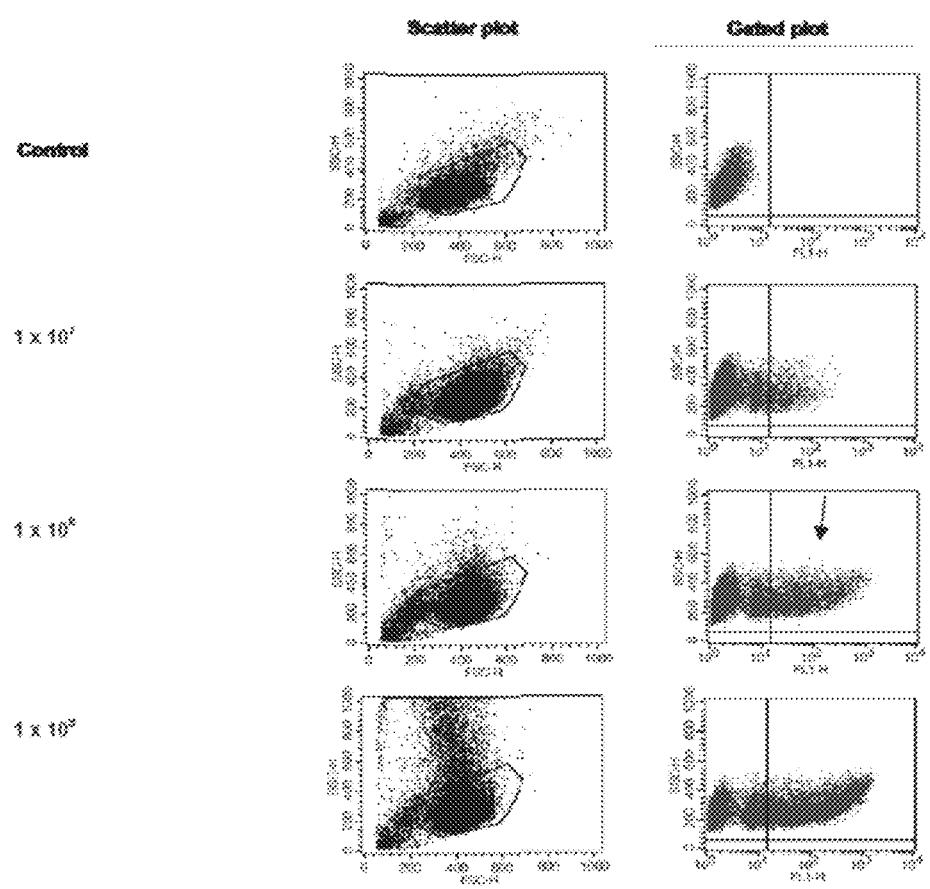
Figure 3B:
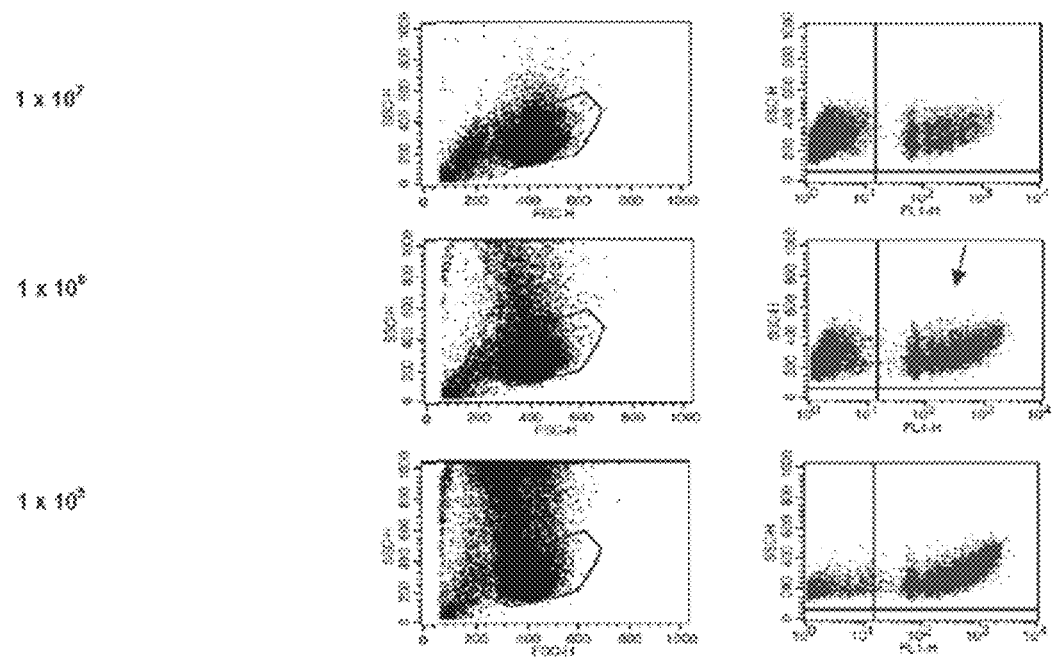
Figure 3C:
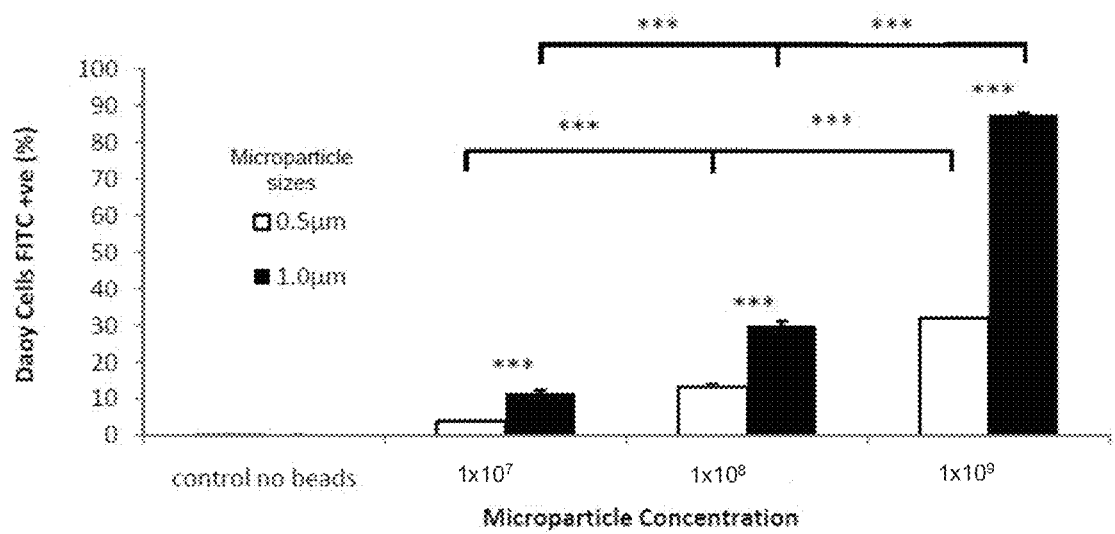

FIGS. 3A-3C show uptake of unmodified synthetic particles in Daoy medulloblastoma cells. (FIGS. 3A-3B) Flow cytometry scatter plots (left) and gated plots (right) for gated Daoy cells: (FIG. 3A) (right) Shows an increase in the population of cells with 0.5 μm microparticles as concentration is increased (greater shift to the upper right quadrant). (Left) There is increased side scatter on the scatter plot at higher concentrations. Control cells have no microparticles and are used as negative controls; (FIG. 3B) (Right) Shows a similar increase in the population of cells with 1.0 μm microparticles when concentration is increased. This is associated with grater side scatter (Left). The population of cells with 1.0 μm microspheres is more distinct than cells with 0.5 μm microparticles at the same concentration. SSC-H side scatter cell; FSC-H=forward scatter cell (size); FL1-H=channel for FITC registering cells with polystyrene dragon green microparticles. (FIG. 3C) Graph illustrating the uptake of microparticles by ND7/23 cells at different concentration and sizes (summarised from flow cytometry data). There is no significant difference in the uptake between the sizes at the same concentration ($p>0.05$) (ns) in each case (not size dependent). There is no difference in uptake between $1\times10^7$ and $1\times10^8$ concentrations of 0.5 μm although the difference between $1\times10^8$ and $1\times10^9$ concentrations is significant ($p<0.001$)***. There is a significant difference in uptake between $1\times10^7$ and $1\times10^8$ 1.0 μm microparticles ($p<0.05$)* and between $1\times10^8$ and $1\times10^9$ concentrations ($p<0.001$)***. Error bars show SEM, n=3.

Figure 4A:
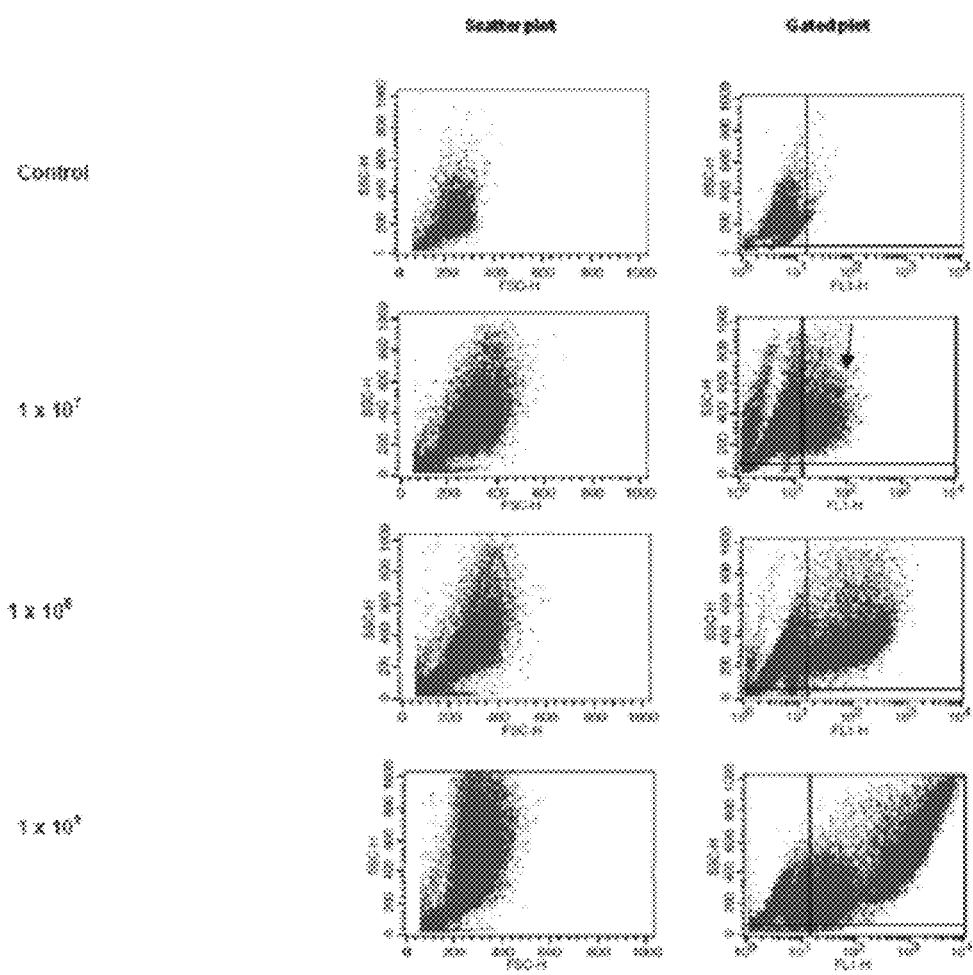
Figure 4B:
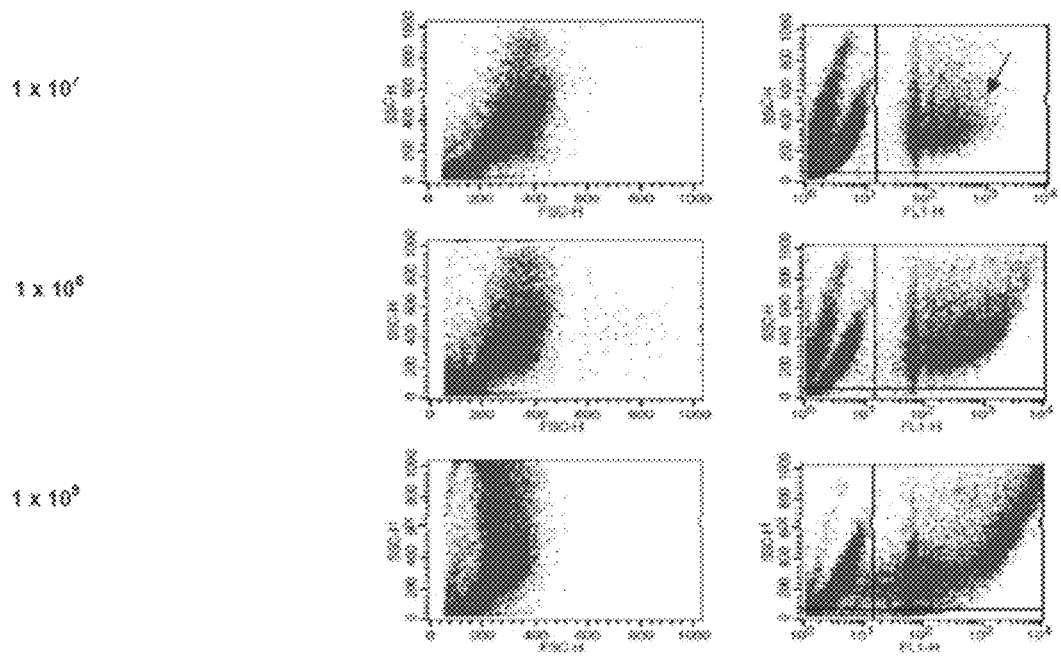
Figure 4C:
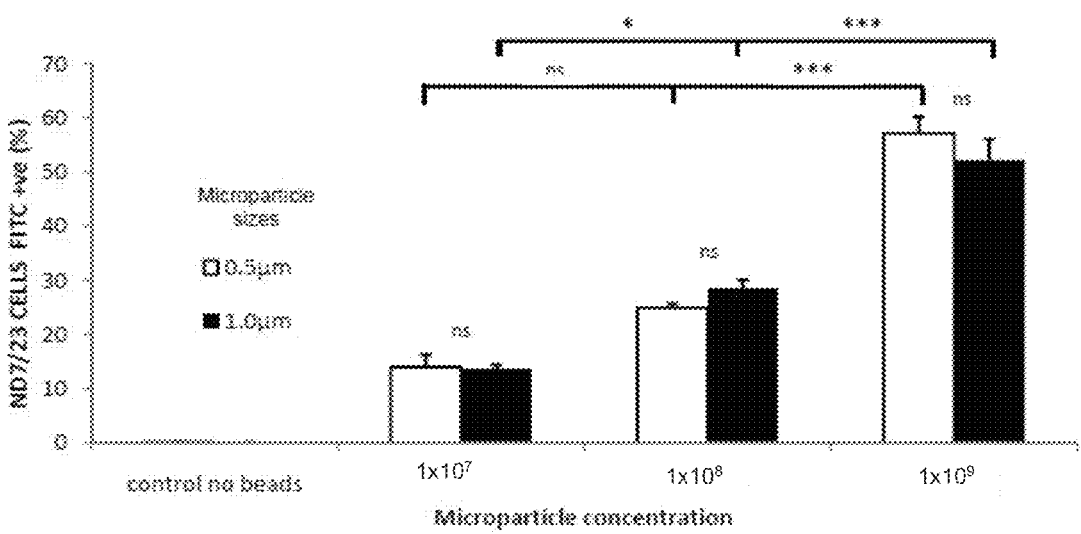

FIGS. 4A-4C show uptake of unmodified synthetic particles in ND7/23 sensory neuron cell line. (FIGS. 4A-4B) Flow cytometry scatter plots (left) and gated plots (right) for ND7/23cells: (FIG. 4A) (right) Shows an increase in the population of cells with 0.5 μm microparticles as concentration is increased (greater shift to the upper right quadrant). (Left) There is increased side scatter on the scatter plot at higher concentrations. Control cells have no microparticles and are used as negative controls. (FIG. 4B) (Right) Shows a similar increase in the population of cells with 1.0 μm microparticles when concentration is increased. This is associated with grater side scatter (Left). The population of cells with 1.0 μm microparticles is more distinct (light arrow) than cells with 0.5 μm microparticles at the same concentration (black arrow). SSC-H=Side scatter cell; FSC-H=forward scatter cell (size); FL1-H=channel for FITC registering cells with dragon green microparticles. (FIG. 4C) Graph illustrating the uptake of microparticles by ND7/23 cells at different concentration and sizes (summarised from flow cytometry data). There is no significant difference in the uptake between the sizes at the same concentration ($p>0.05$) (ns) in each case (not size dependent). There is no difference in uptake between $1\times10^7$ and $1\times10^8$ concentrations of 0.5 μm although the difference between $1\times10^8$ and $1\times10^9$ concentrations is significant (p<0.001)***. There is a significant difference in uptake between $1\times10^7$ and $1\times10^8$ 1.0 µm microparticles (p<0.05)* and between $1\times10^8$ and $1\times10^9$ concentrations (p<0.001)***. Error bars show SEM, n=3.

Figure 5:
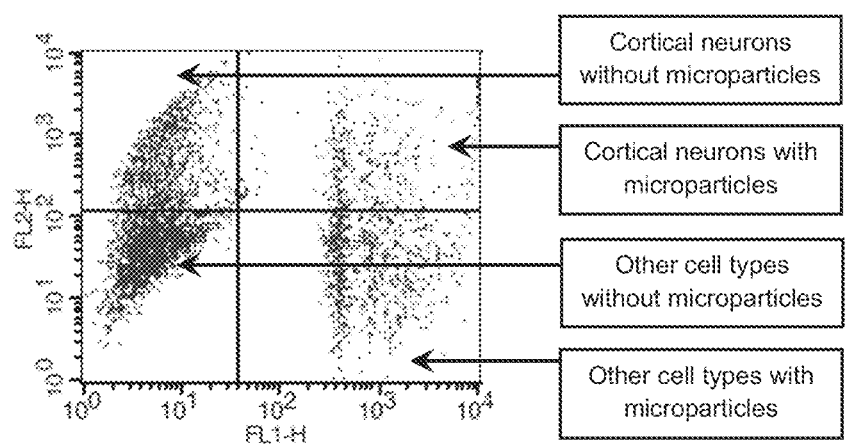

FIG. 5 shows uptake of unmodified synthetic particles in primary cortical neurons and other cell types. This flow cytometry graph plots the fluorescence of PE (FL2-H) against FITC (FL1-H) for a primary cortical culture from mice brains after the addition of polystyrene microparticles over 24 h. CD90.2-PE positive cells (cortical neurons) are seen in the upper right and left quadrants with other cell types (mainly glial cells) seen in the bottom quadrants. Cells that have ingested microparticles are seen in the upper and lower right quadrants. The graph shows that cortical neurons and other cell types also ingest unmodified particles in culture.

Figure 6A:
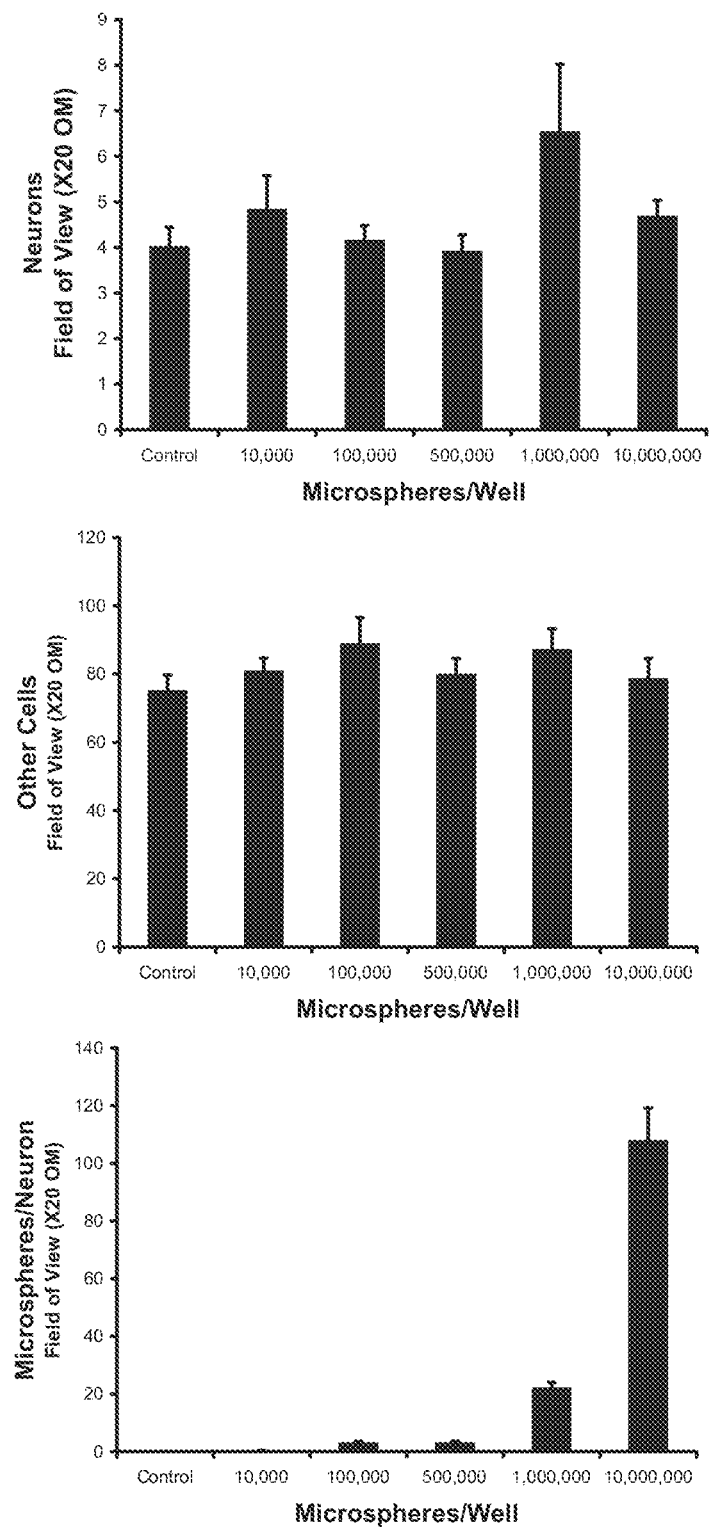
Figure 6B:
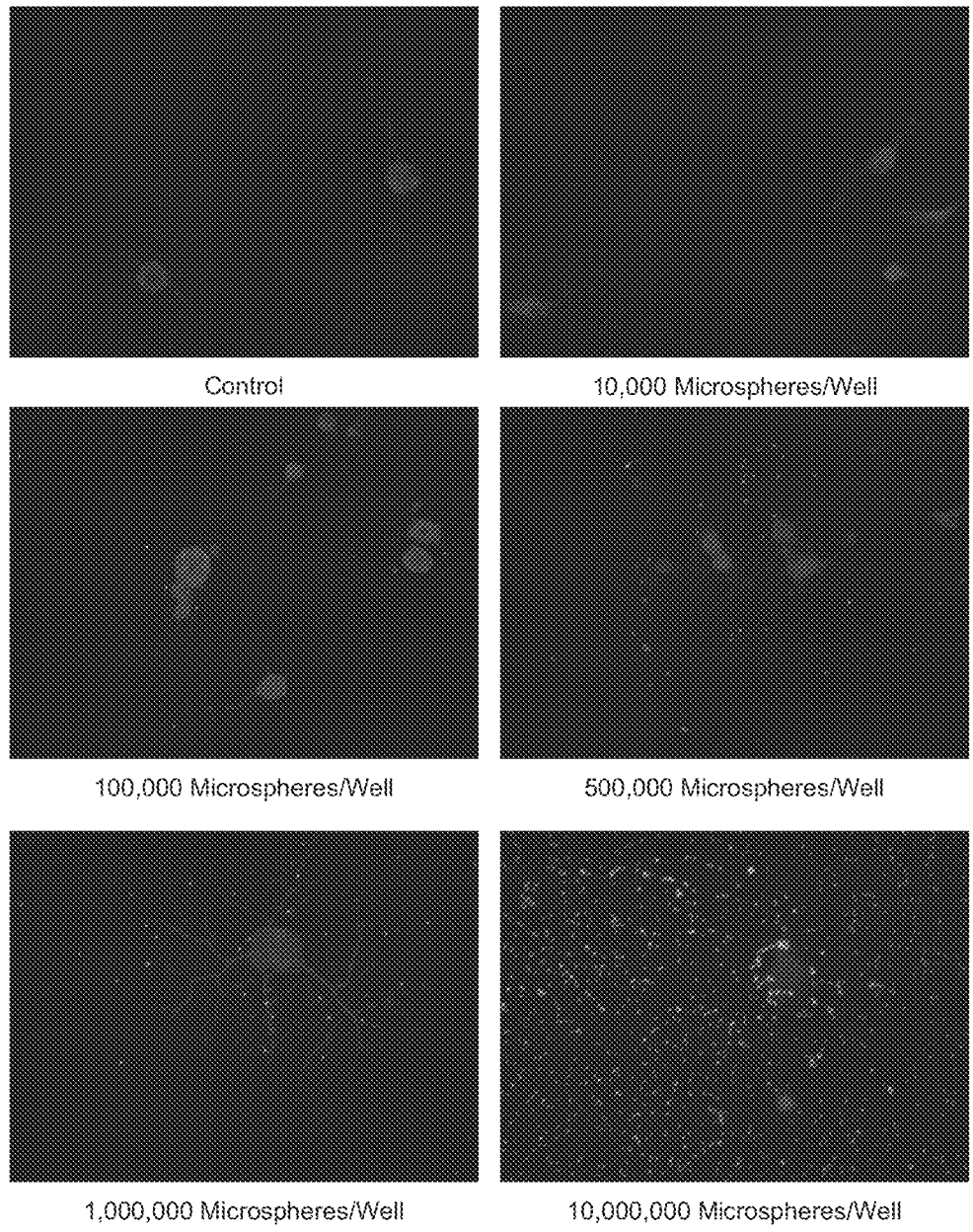

FIGS. 6A-6B show uptake of particles by primary sensory neurons from adult rat and their viability. (FIG. 6A) The number of DRG neurons and other cell types does not vary after the addition of increasing microparticle concentration to the cultures. This suggests that the microparticles do not cause toxicity to the cells. (FIG. 6B) Examples of healthy neurons in increasing concentrations of microparticles (×20 OM).

Figure 7A:
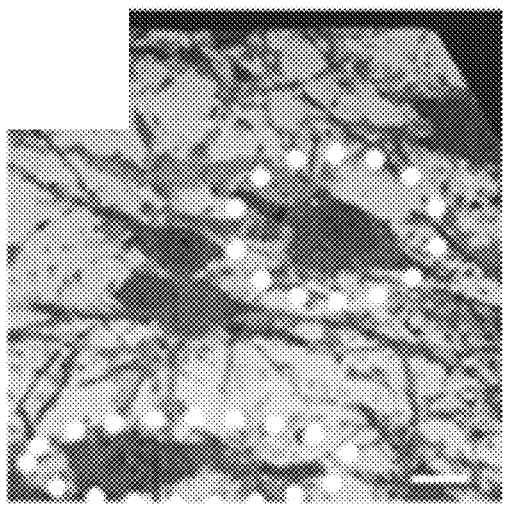
Figure 7B:
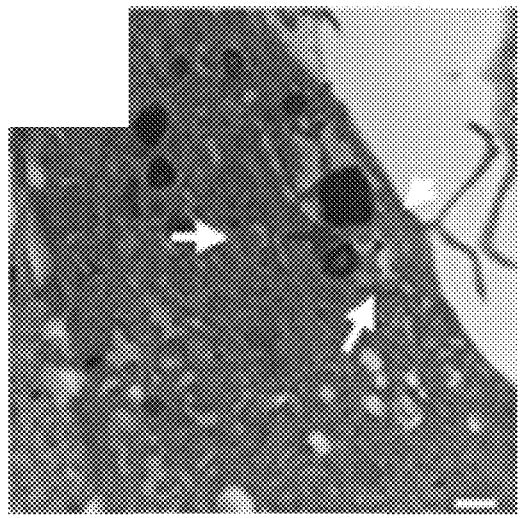
Figure 7C:
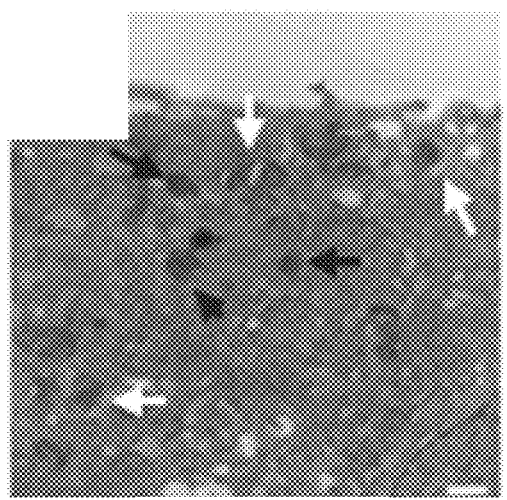
Figure 7D:
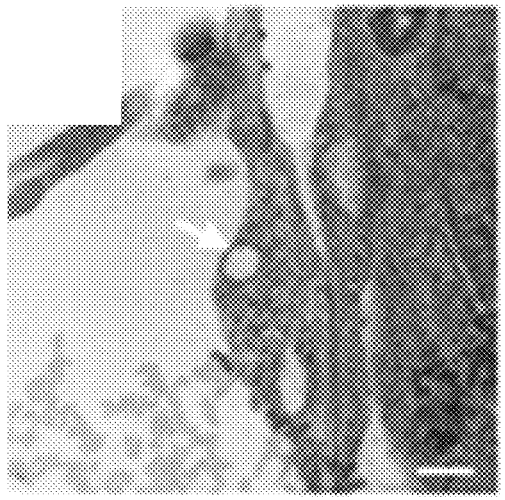
Figure 7E:
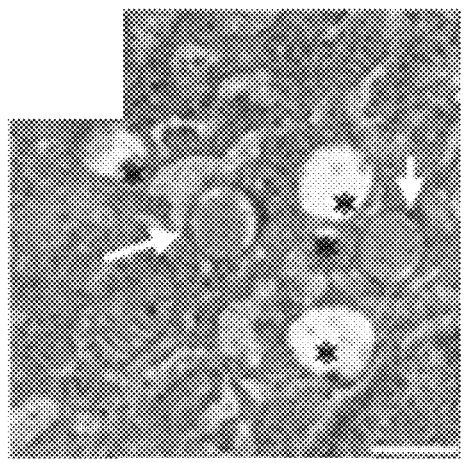
Figure 7F:
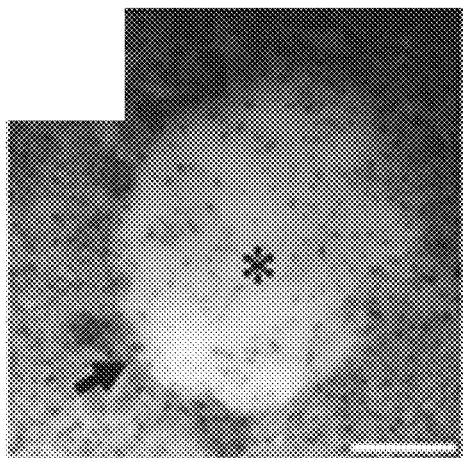
Figure 7G:
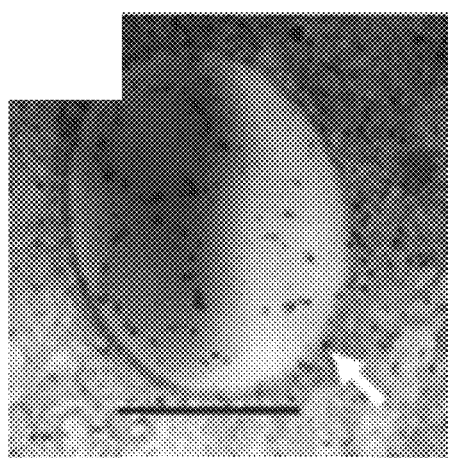
Figure 7H:
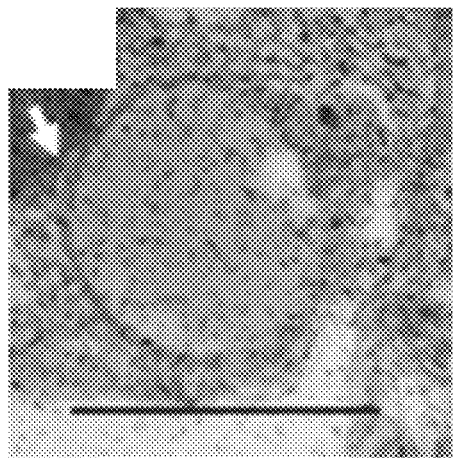
Figure 7I:
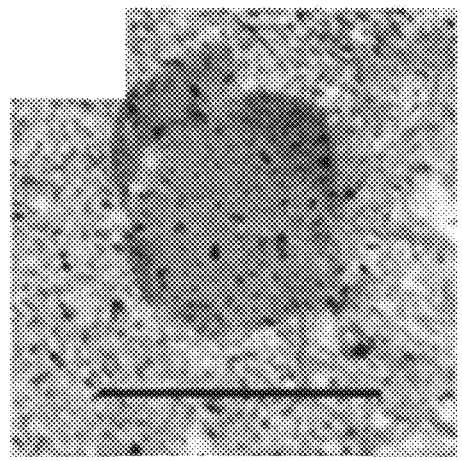
Figure 7J:
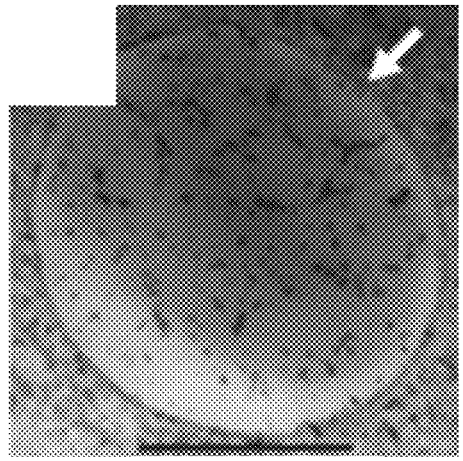
Figure 7K:
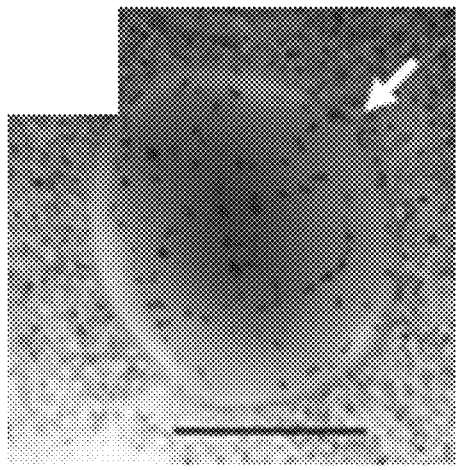
Figure 7L:
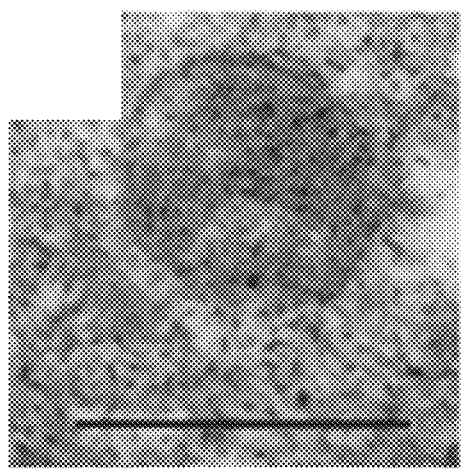
Figure 7M:
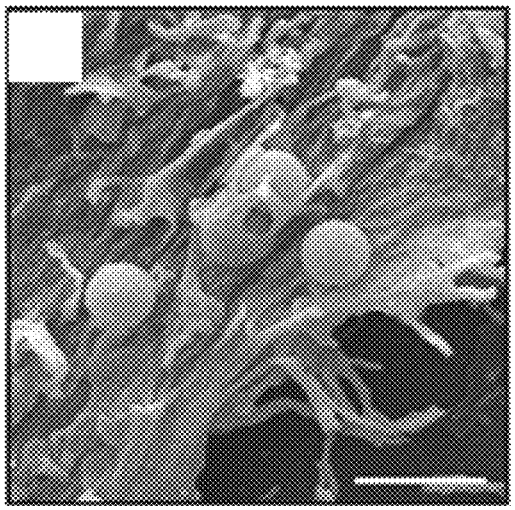
Figure 7N:
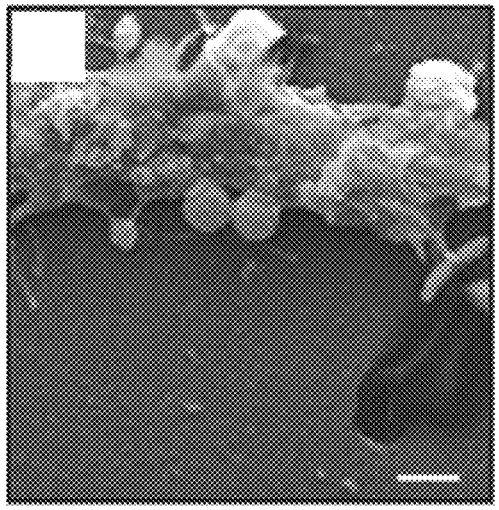
Figure 7O:
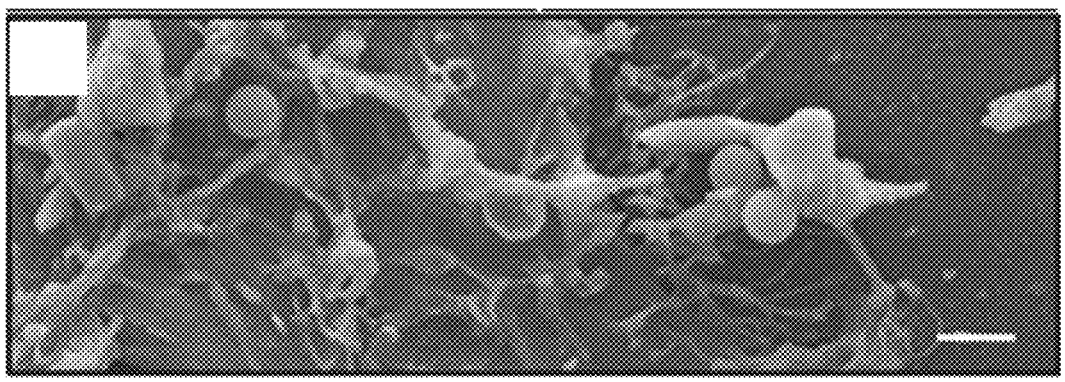

FIGS. 7A-7O show electron microscopy studies do not show toxicity at the ultrastructural level. (FIGS. 7A-7F) Selection criteria for the study of microparticles (MP) in neurons using transmission electron microscopy: (FIG. 7A) Neurons have characteristic long and thin processes. Note the adjacent glial cells with shorter and fatter processes (circled). (FIG. 7B) Membrane bound MP represented by white arrows. There is a small MP in B (arrow). (FIG. 7C) MP not bound by phagosomal membranes (arrows) were not quantified. MP bound by phagosomal membranes are also present (arrows). (FIG. 7D) An empty phagosome in a neuronal process (arrow). FIGS. 7E, 7F: Further examples of empty phagosomes (*) bound by a double membrane (arrow). Bar in A=10 µm, Bar in B-F=0.5 µm. (FIGS. 7G-7L) Transmission electron micrographs of microparticles with and without phagosomal membrane in dorsal root ganglia neurons: (FIG. 7G) Microparticles measuring 0.5 µm within a double membrane phagosome (indicated by arrow). (FIGS. 7H, 7J, 7K) 1 µm microparticles within phagosomes. (FIGS. 7I, 7L) 0.5 µm microparticles that are not bound by phagosomes. Bar=0.5 µm (FIGS. 7M-7O) Scanning electron micrographs of microparticles and dorsal root ganglia: (FIG. 7M) The neuronal membrane has nearly fused to form a vesicle around the microparticles (arrow). (FIG. 7N) Projections of the neuronal membrane around the base of two microspheres. (FIG. 7O) A possible phagocytic cup (arrow) forming where a microparticle can have been dislodged. Bar=1 µm.

Figure 8:
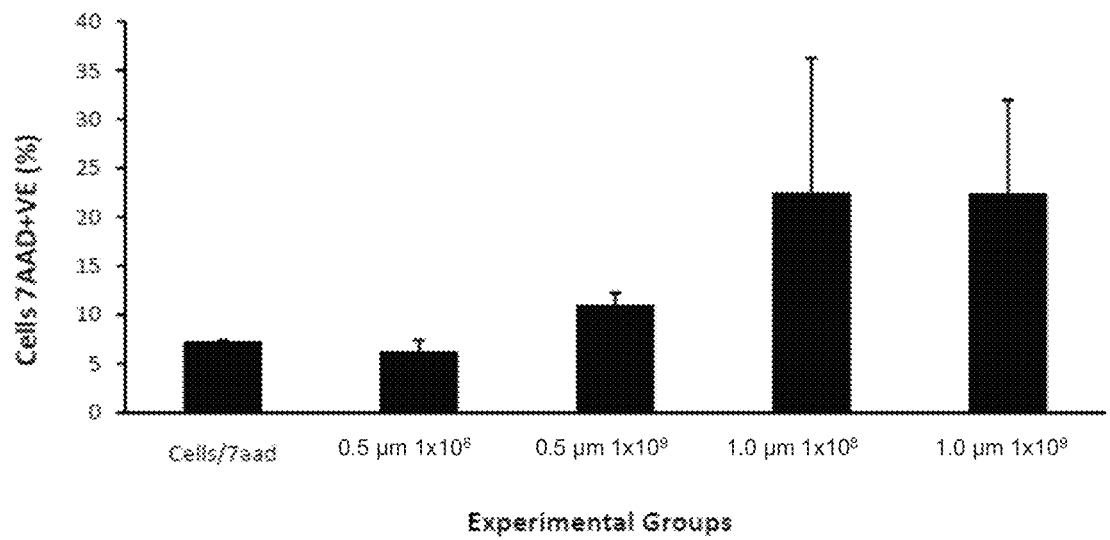

FIG. 8 shows uptake of particles by Daoy human medulloblastoma cell line and their viability. This graph shows total cell death in the different experimental groups. On the X axis are microparticle size and concentration. 1.0 µm microparticles were associated with more cell death compared to 0.5 µm microparticles. Some cell death also occurs in cultures with no microparticles. Data for $H_2O_2$ positive control not included. Error bars show SEM, n=3. The data shows that even for very high concentration of particles (beyond practical use), cell toxicity is limited to below 25%.

Figure 9:
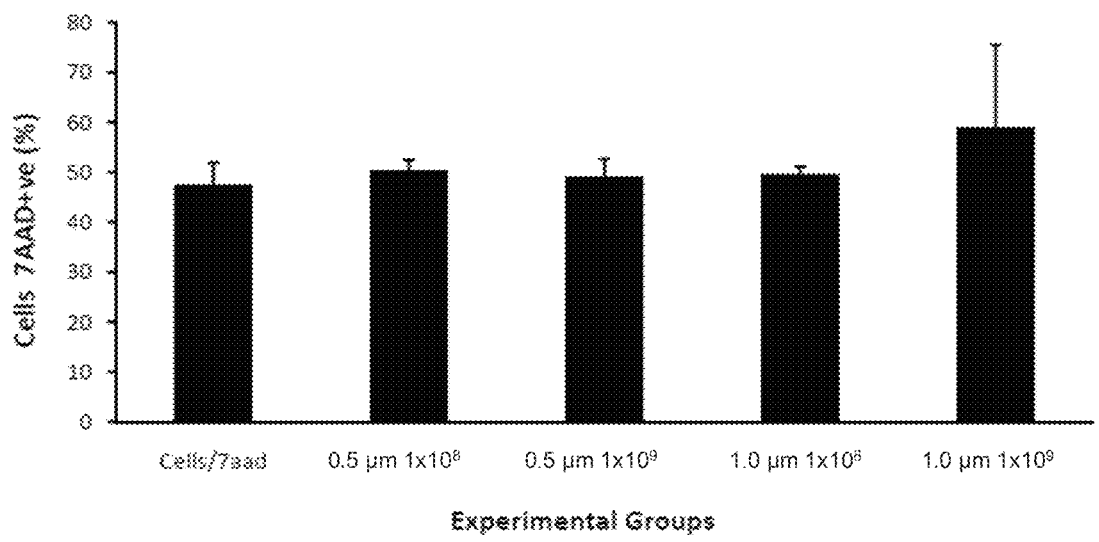

FIG. 9 shows uptake of particles by ND7/23 sensory cell line and their viability. This graph shows total cell death in the different experimental groups. On the X axis are microparticle size and concentration. Cell death is already high in control cultures without microparticles for this cell line and this is not worsened by the addition of microparticles. This graph shows total cell death is relatively constant between the different experimental groups. Error bars show SEM, n=3.

Figure 10:
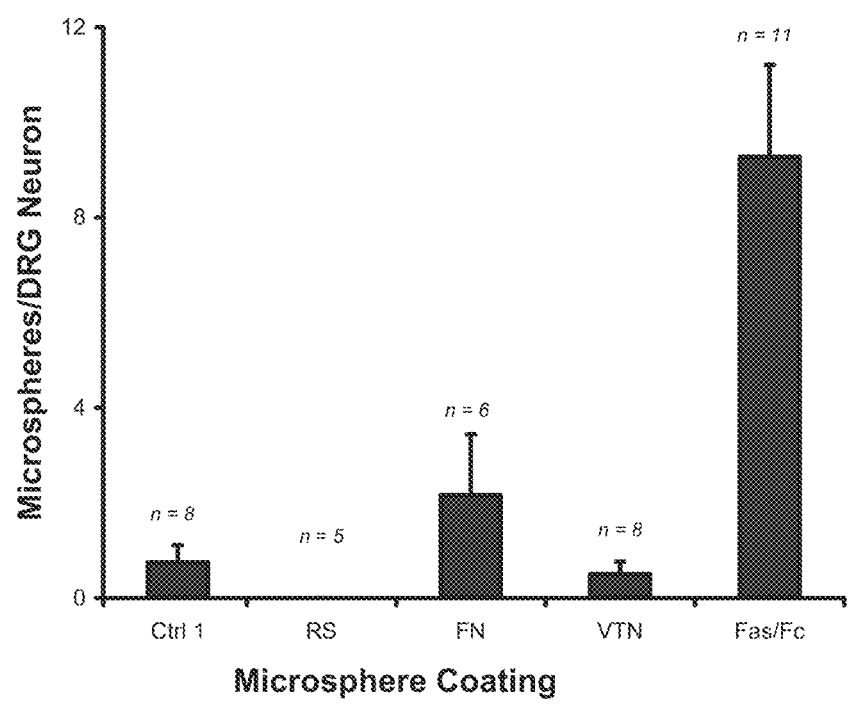

FIG. 10 shows FasFc modified polystyrene particles added to primary DRG neurons. The effect of FasFc modification on the uptake of 1 µm dragon green polystyrene microparticles by DRG neurons was studied by fluorescence microscopy. Rat serum, fibronectin, vitronectin and FasFc modified microparticles were all seeded at the same density as control 1 ($1\times10^5$ microparticles per well). The FasFc modification induced a significant amount of microsphere uptake in neurons compared to controls and other types of ligand.

Figure 11:
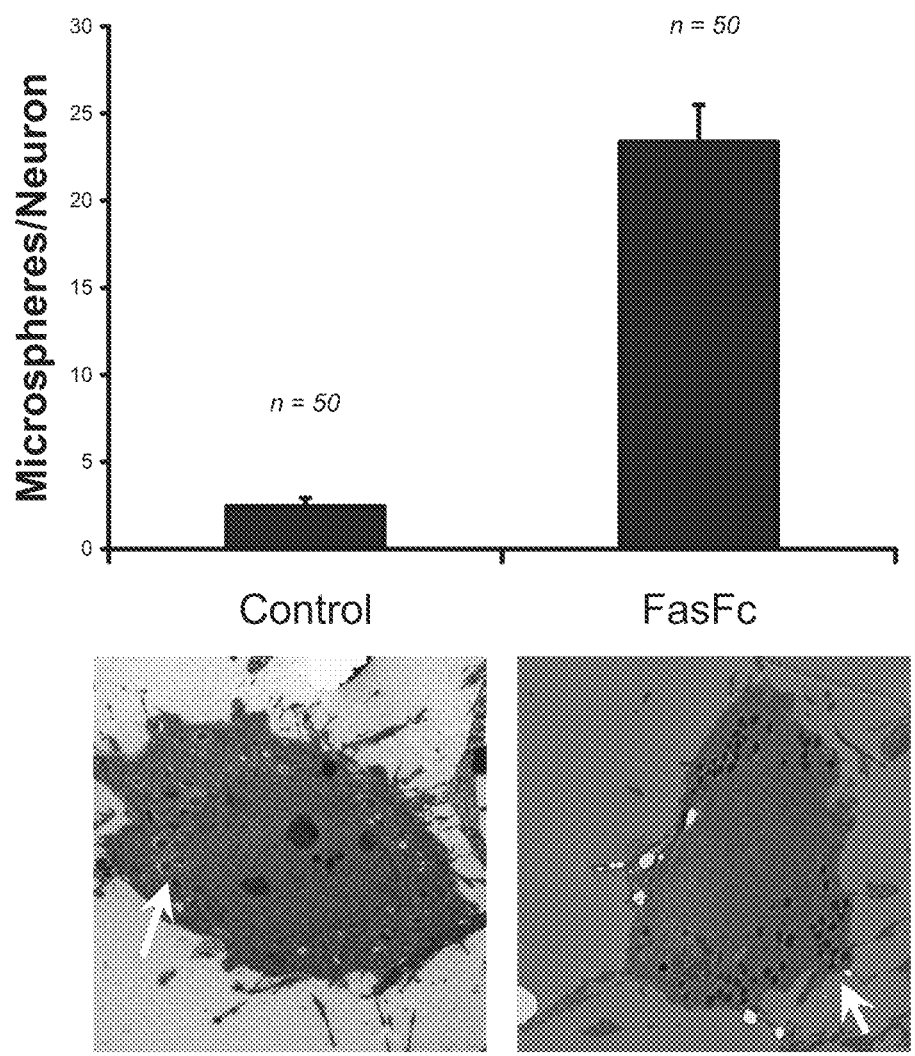

FIG. 11 shows TEM studies of unmodified and FasFc modified particles with DRG neurons. The effect of FasFc modification on the uptake of 1 µm dragon green polystyrene microparticles by DRG neurons was studied by TEM. Unmodified and FasFc modified microparticles were added ($2\times10^6$ microparticles per well) to cultures for 24 h. Ingested microparticles can be seen has electron dense (dark), regular spheres around 1 micron in diameter within the cytoplasm (arrows). The FasFc modification induced a significant amount of microsphere uptake in neurons compared to controls.

Figure 12:
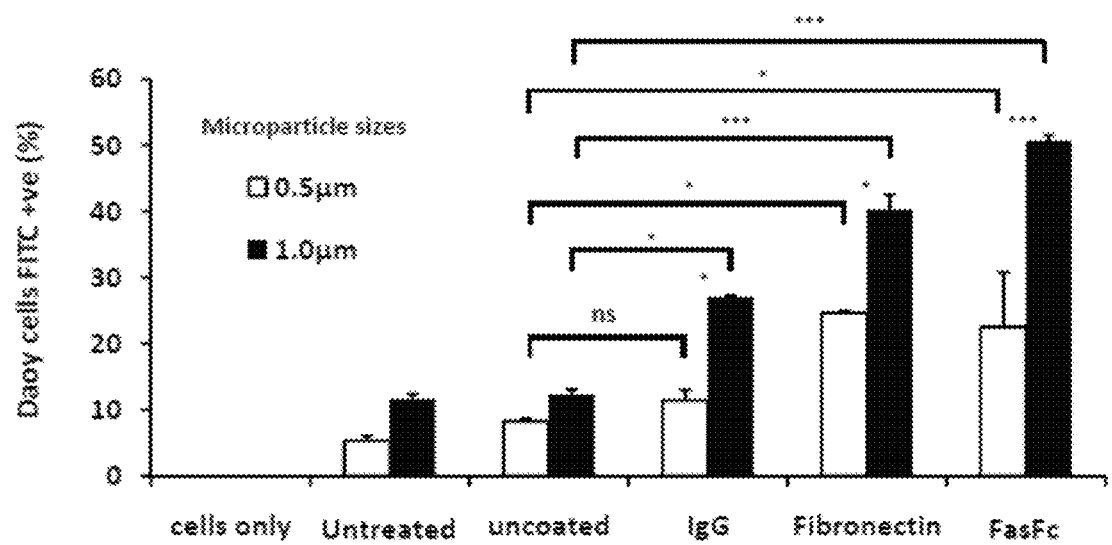

FIG. 12 shows FasFc modified polystyrene particles added to Daoy human medulloblastoma cell line. This graph shows the effect of FasFc microparticle surface modification on uptake compared to uncoated microparticles or particles coated with other ligands for Daoy cells. There was no significant difference in the uptake between untreated microparticles (applied directly to cultures) and uncoated microparticles that underwent coating process in buffer (without a ligand). For the 0.5 µm microparticles there is no significant difference in uptake between uncoated and IgG opsonised microparticles (p>0.05), but there was a significant difference between fibronectin and uncoated (p<0.05)* and FasFc and uncoated (p<0.05)*. For the 1.0 µm microparticles, there was a significant difference between uptake of IgG coated microparticles compared to uncoated controls (p<0.05)*, fibronectin coated compared to uncoated controls (p<0.001)* and FasFc compared to uncoated controls (p<0.001)*. Graph also shows differences in uptake between the sizes. The results also show that Fc rich IgG does not increase the uptake of microparticles to the same extent as FasFc coated microparticles and thus the Fas portion of the fusion protein is key to the increases observed. Error bars show SEM, n=3. $1\times10^7$ microparticles were added per 60 mm Petri dish.

Figure 13:
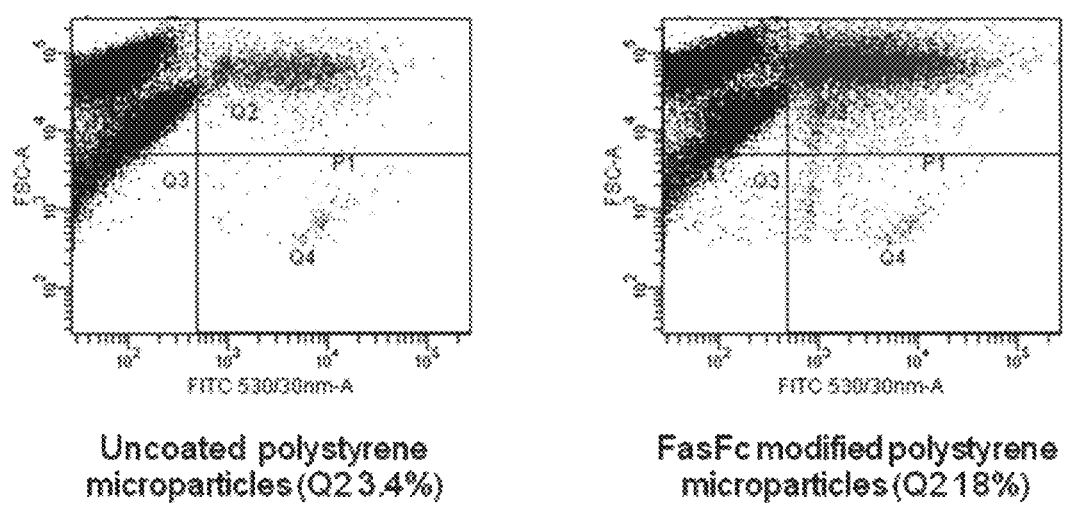

FIG. 13 shows FasFc modified polystyrene particles added to ND7/23 sensory neuron cell line. This graph shows the effect of FasFc microparticle surface modification on uptake compared to uncoated microparticles by ND7/23 cells. The FasFc coated 0.5 µm microparticles were taken up by a much higher percentage of cells (18%) compared to the uncoated microparticles (3.4%) as shown in the upper right quadrants (Q2). $1\times10^5$ microparticles were added per 35 mm Petri dish.

FIGS. 14A-14B show FasFc modified polystyrene particles added to Daoy/cortical neuron co-cultures. These graphs show FasFc microparticle (1 µm) surface modification uptake compared between the Daoy human medulloblastoma cell line and primary cortical neurons from mice after 24 hrs in culture. Daoy cancer cells ingest more particles than cortical neurons and the other cell types in culture (glial cells etc). Experiments were done with P7 cortical neurons (FIG. 14A) and repeated with P14 cortical neurons (FIG. 14B). 1×10$^7$ microparticles were added per 60 mm Petri dish.

FIGS. 15A-15H show intracellular dye delivery using FasFc modified particles added to DRG primary neurons. (FIG. 15A) Merged image (×63 OM), (FIG. 15B) Hoechst stained nuclei, (FIG. 15C) βIII tubulin neuronal marker and (FIG. 15D) ethidium homodimer loaded PLGA particle (diameter <1.2 μm) with no neuronal cytoplasmic staining since they are void of particles (FIG. 15E) Merged image (×63 OM), (FIG. 15F) Hoechst stained nuclei, (FIG. 15G) βIII tubulin neuronal marker and (FIG. 15H) ethidium homodimer loaded PLGA particle with release of nucleic acid dye and labelling of cytoplasmic nucleic acids after 48 hrs.

Figure 16:
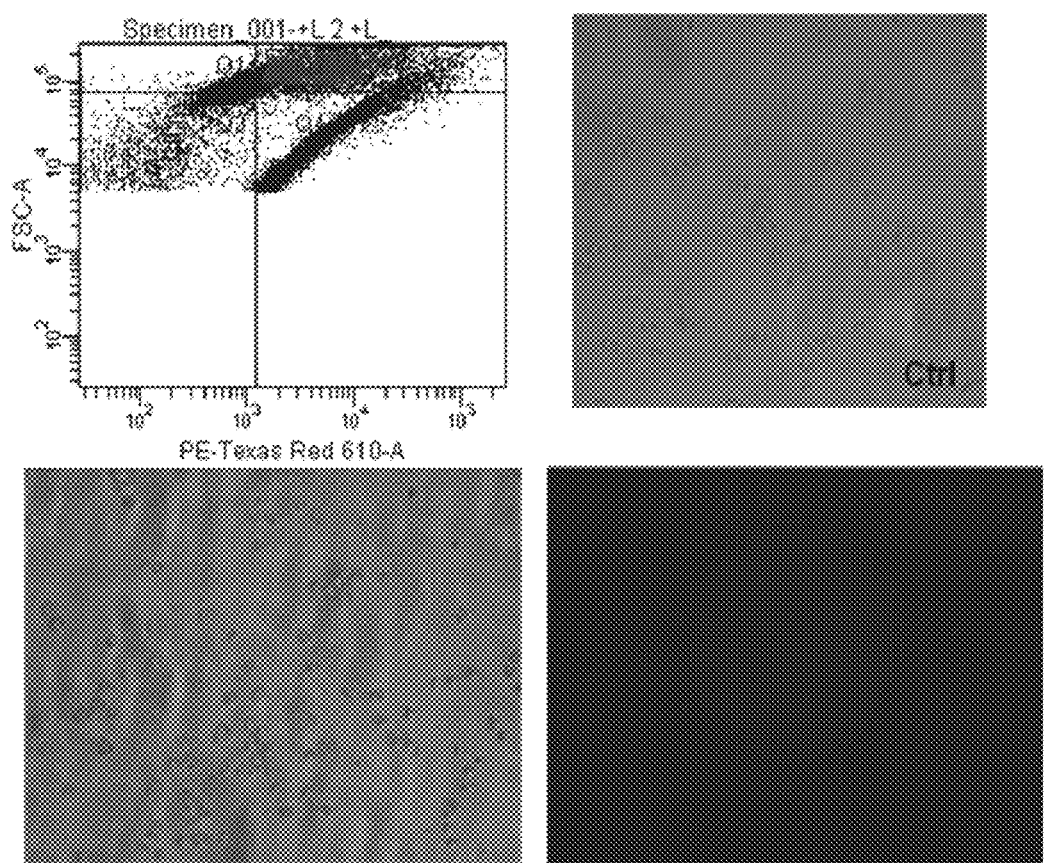

FIG. 16 shows Intracellular drug delivery using FasFc modified particles added to ND7/23 sensory neuron cell line. After overnight addition of FasFc modified particles to ND7/23 cell cultures and separation of cells that ingested doxorubicin loaded particles by FACS (upper left figure), control cells (upper right image) went on to proliferate normally over the next two weeks (observed under the microscope) whereas those cells that ingested doxorubicin loaded particles (on upper left graph; lower images with lower right image showing doxorubicin-loaded particles fluorescence) did not proliferate at all (observed under the microscope for two weeks after separation). These observations show functional drug delivery in the ND7/23 sensory neuron cell line using the invention loaded with the anti-mitotic drug doxorubicin.

Figure 17A:
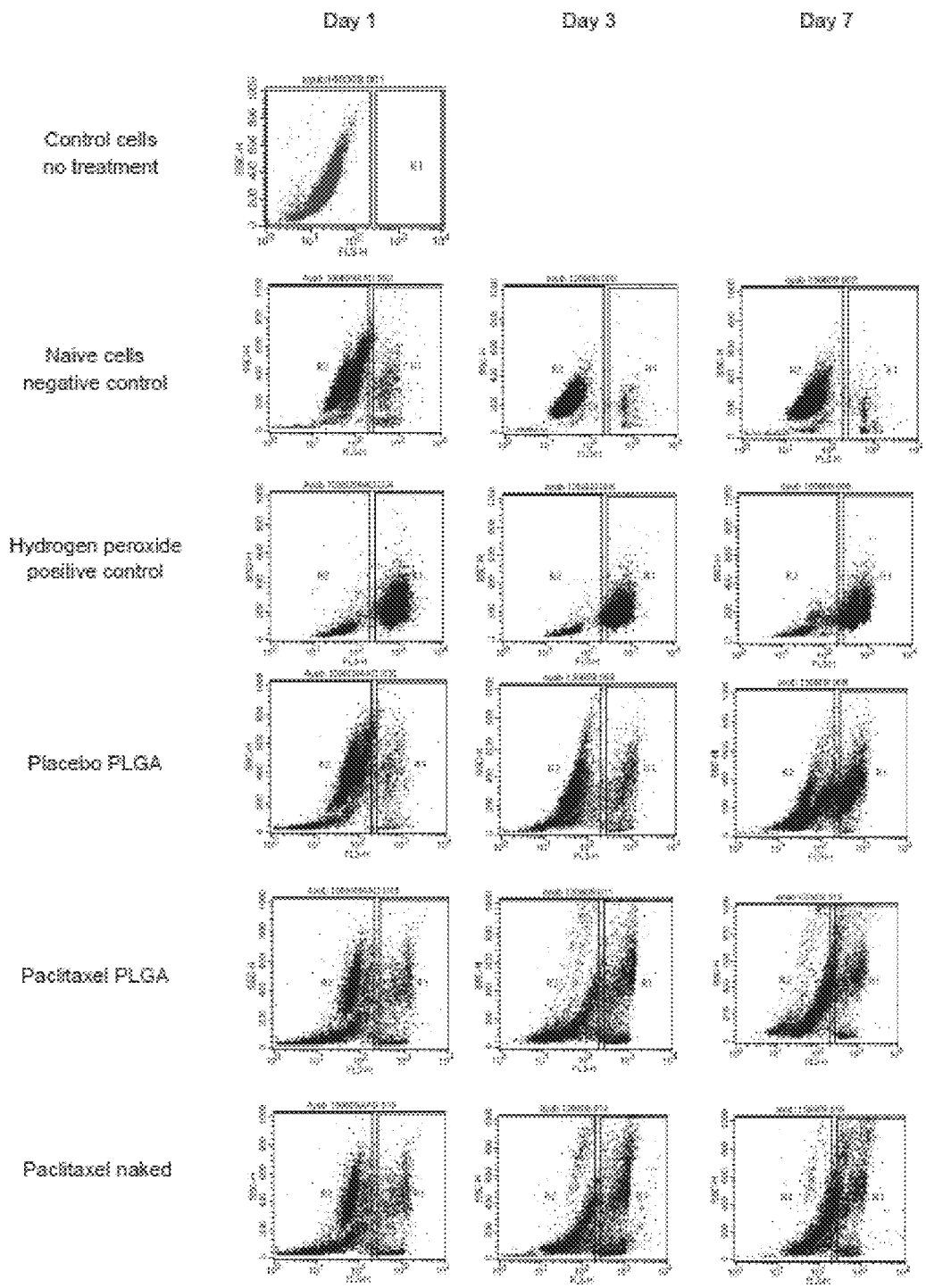
Figure 17B:
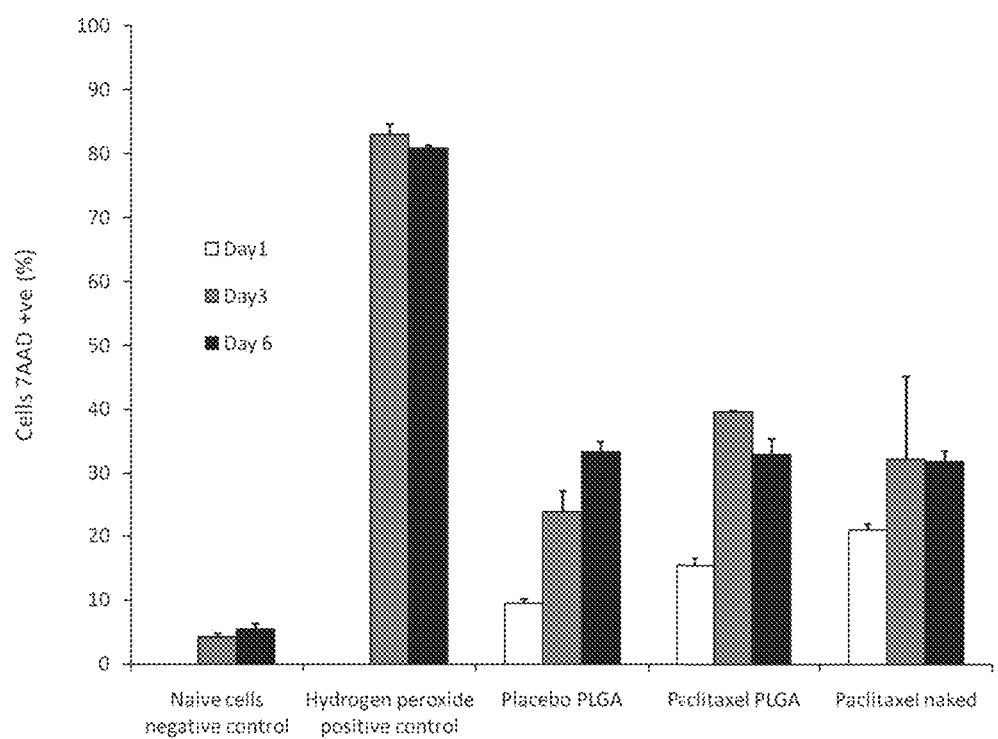

FIGS. 17A-17B show intracellular drug delivery using FasFc modified particles added to Daoy human medulloblastoma cell line. (FIG. 17A) Flow cytometry scatter plots (left) for Daoy cells measuring 7AAD positive cells after addition of 1 μm paclitaxel-loaded PLGA microparticles. Control cells without 7AAD treatment do not register highly in the FL3-H channel (R1 region). Control cells without any drug or placebo treatment show minimal cell death after 7AAD assay. Hydrogen peroxide treated control cells show a high percentage of cell death after 7AAD assay. Functional effects are seen for paclitaxel loaded PLGA microparticles compared to placebo loaded at day 1 & 3, cell death occurs and is comparable to the naked paclitaxel treatment. SSC-H side scatter; FL3-H=channel for 7AAD registering cells. (FIG. 17B) Percentage cell death measured after 7AAD assay (summarised from flow cytometry data). The data shows an increase in cell death for paclitaxel loaded particles at day 1 & 3 compared to placebo. This data demonstrates functional drug delivery in the Daoy medulloblastoma cell line using the invention loaded with pro-apoptotic drug paclitaxel.

FIGS. 18A-18D show FasFc (CD95-Fc) modification enhances the efficacy of paclitaxel-loaded microparticles in vivo. Experiments used poly(lactic-co-glycolic acid) (PLGA) biodegradable microparticles (ca 1.5 μm in diameter) that were either unloaded (placebo) or paclitaxel-loaded at 25% w/w. Microparticles were then surface coated with CD95-Fc or sham coated (−CD95-Fc). (FIG. 18A) Change in tumour volume is shown for an aggressively growing medulloblastoma subcutaneous xenograft. (FIG. 18B) On day 7 after single intratumoral injections, tumour growth was inhibited more efficiently for +CD95 PLGA placebo, −CD95 PLGA paclitaxel and +CD95 PLGA paclitaxel compared to paclitaxel alone. Mean±SEM, n=4. (FIG. 18C) In a murine model of peritoneal ovarian cancer dissemination (IGROV1 luciferase expressing cancer cells), anti-tumour efficacy is shown for +CD95-Fc PLGA paclitaxel compared to an equivalent dose of paclitaxel formulated as Taxol (dissolved in Cremophor EL) after 4 weekly treatment administrations by a >65-fold difference in tumour bioluminescence. Mean±SEM, n=5. Tumour re-growth is relatively slow for the +CD95-Fc PLGA paclitaxel group after suspension of treatment. Both placebo groups had to be sacrificed by day 28 due to extent of disease spread; by day 35, 1 animal in the −CD95-Fc PLGA paclitaxel group was sacrificed; by day 48, a further 2 animals in the −CD95-Fc PLGA paclitaxel, 2 in the paclitaxel and 1 in the +CD95-Fc PLGA paclitaxel group were sacrificed. Statistical comparisons (two-tailed t test) are shown for day 35: paclitaxel vs +CD95-Fc PLGA paclitaxel: *P=0.012; day 35: paclitaxel vs −CD95-Fc PLGA paclitaxel: P=ns; day 41: paclitaxel vs +CD95-Fc PLGA paclitaxel: *P=0.03; day 41: paclitaxel vs −CD95-Fc PLGA paclitaxel: P=ns; day 48: paclitaxel vs +CD95-Fc PLGA paclitaxel: **P=0.0093; day 48: paclitaxel vs −CD95-Fc PLGA paclitaxel: *P=0.02. (FIG. 18D) Live imaging examples for the ovarian cancer study.

EXAMPLE

Materials and Methods
Important Materials
FasFc Chimera—Cat no: F8799-50 ug; Supplier: Sigma Aldrich (UK) Polystyrene fluorescent microparticles: Dragon Green 0.5 μm—Cat no: FS03F/5069; Dragon Green 1.0 μm—Cat no: FS03F/7220; Supplier: Bangs Laboratories (USA) Polylactic-co-glycolic acid (PLGA)—Cat no. Resomer® RG502H; Supplier: Alfa Chemicals (UK)

Cell Line and Primary Cultures
Daoy and ND7/23 cell lines were cultured in DMEM (with glutamine) media with 10% foetal bovine serum (FBS) and 1% penicillin/streptomycin (P/S) at 37° C. and 5% CO2. Cells were plated out into 60 mm dishes, with three dishes per experimental group. ND7/23 cell lines were differentiated with nerve growth factor (NGF) in culture five days before flow cytometry. Daoy cells were cultured without NGF with no additional growth factors required for differentiation.

Dorsal root ganglia (DRGs) sensory neurons were dissected from adult male Wistar rats (2-4 months, >180 g). DRG neurons were cultured in media containing 1% BSA, N2 supplement, NGF and Penicillin-streptomycin at supplier indicated concentrations.

Mice of the C57BL/6 strain was used to obtain cortical neurons (in accordance with Home Office regulations) Cortical neurons were dissected from post-natal days 0-3 mice brains. Cortical neurons were cultured in neurobasal media with 1% horse serum, 1% penicillin—streptomycin and 2% B-27 supplement.

Microparticles were added to cultures and incubated with the cell lines for 24, 48, 72 or 244 hours before further analysis.

Immunofluorescence and Confocal Microscopy Analysis
Immunocytochemically labelled cells were observed directly from well culture slides using microscopy. The Leica DMRD microscope (Leica, UK) was used for fluorescence microscopy only and the Zeiss LSM 510 microscope (Zeiss, UK) was used for confocal analysis. Software attached to the microscopes and Adobe Photoshop 7.0 were used to capture and present images.

Electron Microscopy
For transmission electron microscopy, cells were fixed in 4% glutaraldehyde buffered in phosphate for 1 hour and left in buffer overnight. Cells were post-fixed for 30 minutes with 1% osmium tetroxide. Dehydration was performed in a series of graded Durcupan solution (50, 70, 90, 100 and 100%), a mixture of 100% Durcupan and embedding medium, and pure embedding medium respectively. Ultra-thin sections measuring 70-80 nm were collected on copper grids and stained with uranyl acetate and lead citrate before examination under an accelerating voltage of 80 kV.

For scanning electron microscopy, cells on coverslips were rinsed with phosphate buffer and fixed with 1.5% gluyaraldehyde buffered in phosphate for a minimum of 2 hours. Cells were post-fixed with 1% osmium tetroxide for 1 hour and dehydrated in a series of graded methanol. Cells were then exposed to hexamethydisalizine and left to dry overnight at room temperature. Coverslips were removed, mounted on aluminium stubs and gold coated before being viewed under a 10 kV voltage.

Flow Cytometry

The FACScan flow cytometer (Beckton Dixon) with cell quest software was used for the studies. Cells from each experimental group were prepared as per protocol and transferred in to labelled flow cytometry tubes for analysis. The appropriate gating and controls were used. Cells were detected using appropriate antibodies. For internalisation studies the polystyrene particles were fluorescent in the FITC channel.

7AAD Cell Death Assay

The population of dead cells were identified using the 7AAD (7-Aminoactinmyosin D) assay. H202 was used as the positive control and was added to culture in a final concentration of 100 mM for 4 hours at 37° C. Floating cells were transferred into falcon tubes from each dish and centrifuged preparing cells for flow cytometry. For the 7AAD assay, 10 μl of 7AAD was added to each flow tube and samples analysed to assess cell death.

Microparticle Modification with FasFc

Microparticles were surface modified with fibronectin, vitronectin, rat serum, IgG or FasFc by simple adsorption. They were suspended in 10 μg/200 μl of the respective ligand for a minimum of 90 mins, whilst uncoated microspheres were suspended in the same volume of phosphate buffer saline. The suspension was vortexed every 30 minutes to ensure adequate coating of the microspheres. It is also possible to modify the microparticles using various chemical conjugation techniques or the ligands can be incorporated in the matrix of biodegradable microparticles.

Drug-Loaded Microparticles

Doxorubicin or paclitaxel-loaded PLGA microparticles were synthesised using the standard double emulsion technique. PLGA (RG502H, Boehringer Ingelheim, Germany) placebo (unloaded) microspheres were prepared by a single emulsion solvent evaporation technique, microsieve emulsification. Prior to emulsification a 7% w/v PLGA solution in dichloromethane was filtered through a 0.2 μm PTFE filter. Thereafter the PLGA was emulsified through a microsieve membrane (Nanomi BV, The Netherlands), which is a microfabricated membrane with uniform pores along the surface, into an aqueous solution containing an emulsifier. The resultant emulsion was left to stir at room temperature for at least three hours to evaporate the solvent. The hardened microspheres were concentrated by filtration and washed repeatedly. Subsequently, the particles were freeze-dried and stored at −20° C. until evaluation. For paclitaxel loaded PLGA (RG502H, Boehringer Ingelheim, Germany) microspheres, paclitaxel was added and dissolved into a 6% w/v PLGA solution in dichloromethane in order to achieve a final microparticle drug concentration of 25% w/w. The solution was filtered through a 0.2 μm PTFE filter and emulsified through a silicon microsieve. Ultrapure water containing an emulsifier was used as continuous phase. The emulsion was magnetically stirred for at least 3 hours at room temperature to evaporate dichloromethane. After solidification microspheres were also collected by filtration and washed repeatedly. Subsequently, the particles were freeze-dried and stored at −20° C. until evaluation. Uniform sized paclitaxel loaded and placebo microparticles (around 1.5 μm) were obtained from Nanomi BV (The Netherlands).

Ovarian Cancer Xenograft $5 \times 10^6$ IGROV1-luciferase cells were inoculated IP into female Balb C nu/nu mice on day 1. Paclitaxel (20 mg/kg) and PLGA microspheres were administered IP once per week (days 7, 14, 21 and 28). For bioluminescence imaging, mice were injected IP with 125 mg/kg D-luciferin (Calliper Life Sciences, UK) and then anesthetized (2% isofluorane by inhalation). Five minutes later, whilst still under anaesthetic, they were placed in a light-tight chamber on a warmed stage (37° C.) and light emission from a defined region of interest on a ventral surface was imaged on a Xenogen IVIS Imaging System 100 system (Alameda, Calif., USA). Data were analyzed using Living Image software (also Xenogen, Alameda, Calif., USA) and are presented as relative radiance (calculated from mean Radiance photons/s/cm2/sr)."

Statistical Analysis

Standard error of mean (SEM) was used to assess consistency between each experimental group. One way ANOVA with Bonferroni post test were used to evaluate differences between groups. Two tailed t test was used to compare two groups.

Results

Uptake of Unmodified Polystyrene Particles in Non-Professional Phagocytes

The inventors have previously demonstrated the ability of neurons to take up microparticles and debris in vitro and in vivo (Bowen et al., 2007). The FIGS. 1 & 2 show examples of this in primary sensory neuron cultures in the case of polystyrene particles and also included are previously unpublished data for another drug delivery system; polyelectrolyte capsules. The inventors also show the uptake of unmodified synthetic particles by other cells including the Daoy human medulloblastoma cell line (FIG. 3), ND7/23 sensory neuron cell line (FIG. 4) and primary cortical neurons (FIG. 5) by flow cytometry experiments.

Toxicity Studies of Unmodified Polystyrene Particles

These studies looked at the effect of adding unmodified 1 μm polystyrene (PS) microspheres on the viability of various cell types. Microspheres were added in increasing concentrations and the number of DRG neurons, other cells per field of view were quantified after 24 h (FIG. 6). The essential observation for this model was that no reduction in cell numbers was seen in the presence of microspheres, even at extremely high concentrations. This suggests that the uptake of particles in these cultures does not result in any significant toxicity. This was also confirmed in independent repeat experiments including detailed ultrastructural studies by transmission and scanning electron microscopy (FIG. 7). Flow cytometry experiments using the Daoy human medulloblastoma cell line (FIG. 8) and the ND7/23 sensory neuron cell line (FIG. 9) looked at the effect on cell viability with the 7-AAD cell death assay.

Uptake Studies Using Fasfc Modified Polystyrene Particles

The surface modification of particles with the FasFc fusion protein resulted a significant increase in the uptake of particles by certain types of neuronal and cancer cells. FIG.

10 demonstrates this increase compared to controls and modification with other ligands for dorsal root ganglion primary neurons. These results strongly demonstrate the improvement in neuronal particle uptake that is achieved with the invention. Studies using transmission electron microscopy (FIG. 11) confirmed these results in dorsal root ganglion primary neurons. Further exemplification in the Daoy human medulloblastoma cell line (FIG. 12) and the ND7/23 sensory neuron cell line (FIG. 13) showed the ability to increase uptake in certain cell types by using FasFc modified particles. Furthermore, in co-cultures of Daoy human medulloblastoma cells with mouse cortical neurons, the preferential uptake of particles by Daoy cells compared to cortical neurons is seen, showing utility in the treatment of brain tumours (FIG. 14).

Cytoplasmic Drug Delivery Using Fasfc Modified PLGA Particles

Polylactic-co-glycolic acid (PLGA) biodegradable particles were synthesised using the established double emulsion method or particles from Nanomi BV (The Netherlands) using their proprietary Microsieve™ technology (www.nanomi.com). During synthesis a range of pharmaceutically active agents or markers can be incorporated into the particles including small molecules, peptides, proteins and nucleic acids. The inventors exemplified our invention using microparticles incorporating the ethidium homodimer nucleic acid dye and the anti-cancer drugs doxorubicin and paclitaxel. The inventors have shown that ethidium homodimer loaded PLGA with a FasFc modification enhances the uptake and subsequent delivery of agent (FIG. 15H) with no cytoplasmic nucleic acid staining seen in control cells without ingested particles (FIG. 15D). When unmodified control particles were added to controls no examples of uptake and agent delivery could be found. Similarly, the inventors added doxorubicin loaded PLGA particles to ND7/23 cells, and after cell separation with FACS, cell proliferation was inhibited in those that ingested doxorubicin loaded particles (FIG. 16). When paclitaxel loaded particles were added to Daoy human medulloblastoma cells, a functional effect as for the naked drug was seen at day 1 and 3 for paclitaxel loaded particles compared to unloaded placebo particles (FIG. 17). These results demonstrate the utility of this invention in drug delivery applications.

Figure 18A:
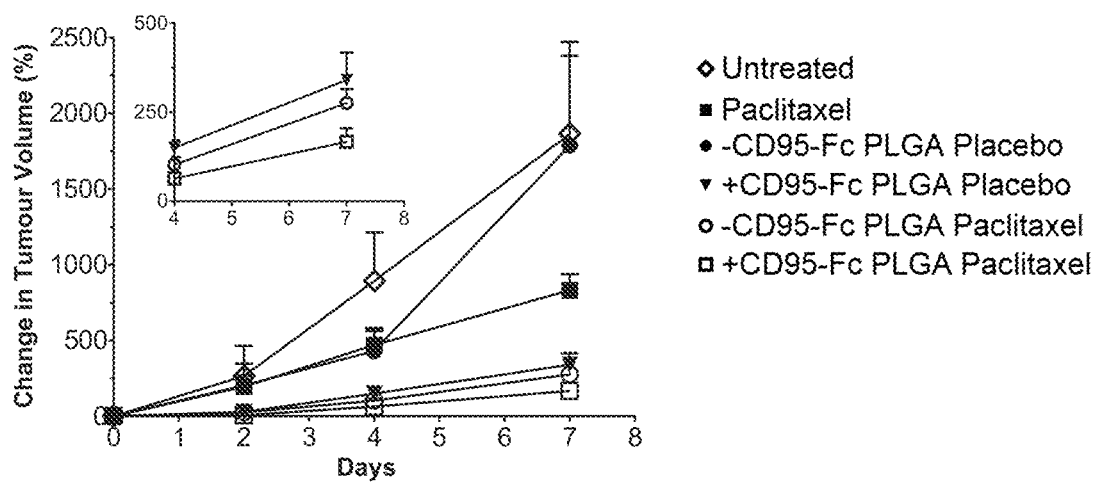
Figure 18B:
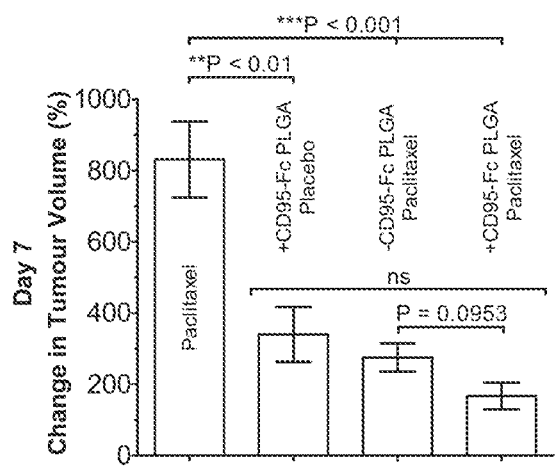
Figure 18C:
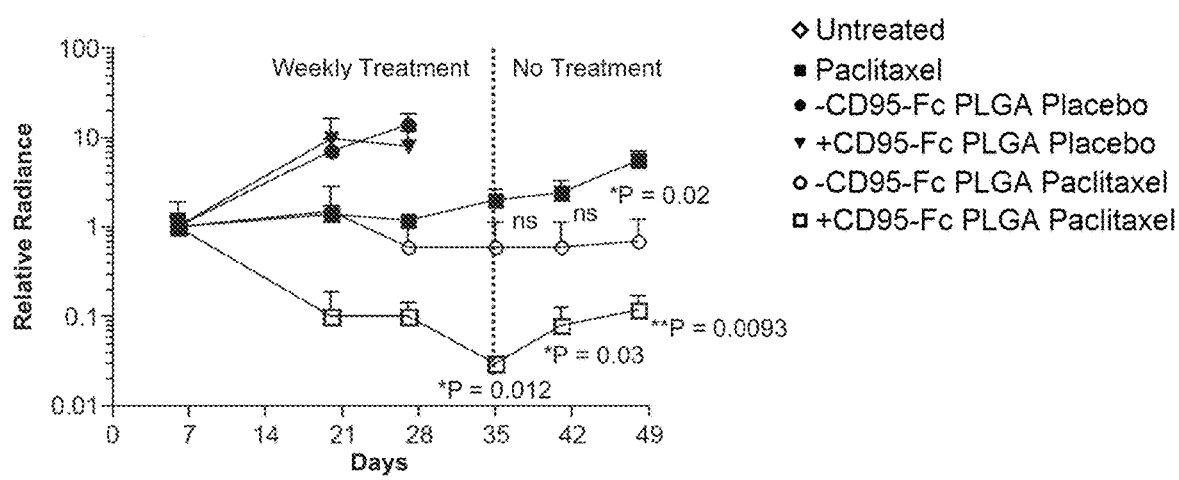
Figure 18D:
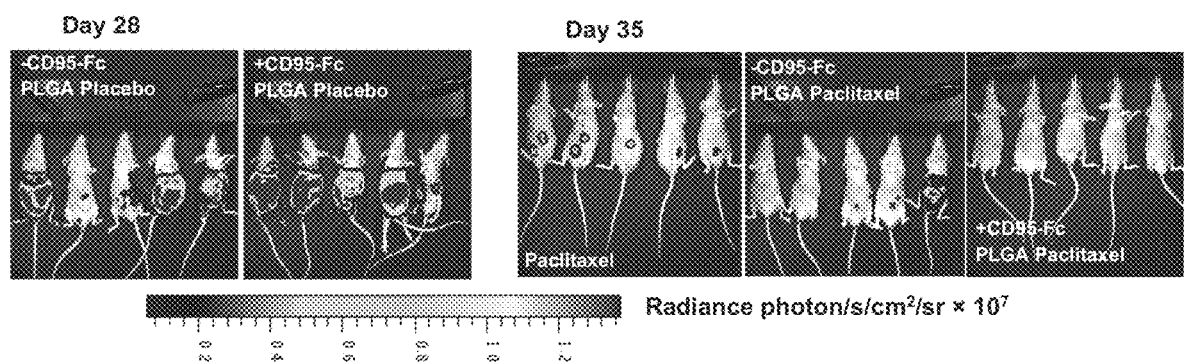

FasFc (CD95-Fc) Modification Enhances the Efficacy of Paclitaxel-Loaded Microparticles In Vivo Moving to a more clinically relevant scenario, the inventors used an orthotopic ovarian cancer model to target CD95L expressing IGROV1-luciferase cells within a compartmentalised space in the presence of other competing cell types (e.g. macrophages) by intraperitoneal injection (FIG. 18C, D). Live imaging showed a >65-fold reduction in tumour bioluminescence by week 4 (FIG. 18C) for the +CD95-Fc PLGA paclitaxel treated group compared with an equivalent dose of Taxol, the clinical standard-of-care therapy (paclitaxel dissolved in Cremophor EL). Unmodified (−CD95-Fc) PLGA paclitaxel matched Taxol. In this model, both placebo treatments (+CD95-Fc & −CD95-Fc) were ineffective. The significant tumour reduction effect for +CD95-Fc PLGA paclitaxel treatment persisted after treatment suspension (FIG. 18C). Mice in this group all survived up to day 48 and at day 62 termination 80% asymptomatic animals remained (data not shown). Previous studies have underlined the potential to inhibit tumour growth using reformulated paclitaxel at high doses. There is also a shift away from intravenous therapy towards intraperitoneal delivery of ovarian cancer drugs in the clinical setting, due to a reported 25% reduction in risk of death. It is rare however, to find reductions in tumour burden at normal doses as reported here. The data strongly support an important role for CD95 modified drug-loaded microparticles for enhanced targeted intracellular drug delivery in ovarian cancer. This is an important area of clinical need, since therapeutic success is hard to achieve in advanced stages of ovarian cancer.

REFERENCES

Abrahams V M, Straszewski S L, Kamsteeg M, Hanczaruk B, Schwartz P E, Rutherford T J and Mor G. Epithelial ovarian cancer cells secrete functional Fas ligand. Cancer Res 2003; 63:5573-5581

Ackery A, Robins S, and Fehlings M G. Inhibition of Fas-mediated apoptosis through administration of soluble Fas receptor improves functional outcome and reduces posttraumatic axonal degeneration after acute spinal cord injury. J Neurotrauma 2006; 23:604-616

Benita, et al., J. Pharm. Sci. 73, 1721-1724 (1984) Bowen S, Ateh D D, Deinhardt K, Bird M M, Price K M, Baker C S, Robson J C, Swash M, Shamsuddin W, Kawar S, El-Tawil T, Roos J, Hoyle A, Nickols C D, Knowles C H, Pullen A H, Luthert P J, Weller R O, Hafezparast M, Franklin R J M, Revesz T, King R H M, Berninghausen O, Fisher EMC, Schiavo G, Martin J E. The phagocytic capacity of neurons. Eur J of Neurosci 2007; 25:2947-2955

Brandhonneur N, Chevanne F, Vié V, Frisch B, Primault R, Le Potier M F, Le Corre P. Specific and non-specific phagocytosis of ligand-grafted PLGA microspheres by macrophages. Eur J Pharm Sci 2009; 36:474-85

Choia C and Benveniste E N. Fas ligand/Fas system in the brain: regulator of immune and apoptotic responses. Brain Res Rev. 2004; 44:65-81

Esselens C, Oorschot V, Baert V, Raemaekers T, Spittaels K, Serneels L, Zheng H, Saftig P, De Strooper B, Klumperman J and Annaert W. Presenilin 1 mediates the turnover of telencephalin in hippocampal neurones via autophagic degradative pathway. J Cell biol 2004; 166:1041-1054

Ethell D W, Kinloch R and Green D R. Metalloproteinase shedding of Fas ligand regulates beta-amyloid neurotoxicity. Curr Biol 2002; 12:1595-1600

Faraji A H and Wipf P. Nanoparticles in cellular drug delivery. Bioorganic Med Chem 2009; 17:2950-2962

Farokhzad O C, Cheng J, Teply B A, Sherifi I, Jon S, Kantoff P W, Richie J P and Langer R. Targeted nanoparticle-aptamer bioconjugates for cancer chemotherapy in vivo. PNAS 2006; 103:6315-6320

Ferguson T A and Griffith T S. A vision of cell death: Fas ligand and immune privilege 10 years later. Immunol Rev. 2006; 213:228-238

Flügel A, Schwaiger F W, Neumann H, Medana I, Willem M, Wekerle H, Kreutzberg G W and Graeber, M B. Neuronal FasL induces cell death of encephalitogenic T lymphocytes. Brain Pathol 2000; 10:353-364.

Giteau A, Venier-Julienne M C, Aubert-Pouëssel A, Benoit J P. How to achieve sustained and complete protein release from PLGA-based microparticles? Int J Pharm 2008; 350:14-26

Gratas C, Tohma Y, Van Meir E G, Kleinz M, Tenans M, Ishii N, Tachibana O, Kleihues P and Ohgaki H. Fas ligand expression in glioblastoma cell lines and primary astrocytic brain tumors. Brain Pathol 1997; 7:863-869

Green D R and Ferguson T A. The role of Fas ligand in immune privilege. Nat Rev Mol Cell Biol. 2001; 2:917-24

Grimm D. Small silencing RNAs: state-of-the-art. Adv Drug Deliv Rev 2009; 61:672-703

Gu F, Langer R and Farokhzad O C. Formulation/Preparation of functionalized nanoparticles for in vivo targeted drug delivery. Methods Mol Biol 2009; 544:589-98

Huwyler J, Drewe J and Krähenbuhl S. Tumor targeting using liposomal antineoplastic drugs. Int J Nanomedicine 2008; 3:21-9

Landau A M, Luk K C, Jones M L, Siegrist-Johnstone R, Young Y K, Kouassi E, Rymar V V, Dagher A, Sadikot A F and Desbarats J. Defective Fas expression exacerbates neurotoxicity in a model of Parkinson's disease. J Exp Med 2005; 202:575-581

Lettau M, Paulsen M, Kabelitz D, Janssen O. Storage, expression and function of Fas ligand, the key death factor of immune cells. Curr Med Chem. 2008; 15:1684-1696

Mello C C and Conte Jr D. Revealing the world of RNA interference. Nature 2004; 431:338-342

Meng Y, Graves L, Do T-V, So J, Fishman D A. Upregulation of FasL by LPA on ovarian cancer cell surface leads to apoptosis of activated lymphocytes. Gynecologic Oncology 2004; 95:488-495

Mathiowitz and Langer, J. Controlled Release 5,13-22 (1987) Mathiowitz, et al., Reactive Polymers 6, 275-283 (1987) Mathiowitz, et al., J. Appl. Polymer Sci. 35, 755-774 (1988) Mathiowitz, et al., Scanning Microscopy 4, 329-340 (1990) Mathiowitz, et al., J. Appl. Polymer Sci. 45, 125-134 (1992)

Muñoz Javier A, del Pino P, Bedard M F, Ho D, Skirtach A G, Sukhorukov G B, Plank C and Parak W J. Photoactivated release of cargo from the cavity of polyelectrolyte capsules to the cytosol of cells. Langmuir 2008; 24:12517-12520

Nagata S and Suda T. Fas and Fas ligand: Ipr and gld mutations. Immunol Today. 1995; 16:39-43

Nagata S. Apoptosis by Death Factor. Cell 1997; 88:355-365

Niehans G A, Brunner T, Frizelle S P, Liston J C, Salerno C T, Knapp D J, Green D R, and Kratzke R A. Human Lung Carcinomas Express Fas Ligand. Cancer Res 1997; 57:1007-1012

O'Connell J, Bennett M W, O'SULLIVAN GC, Roche D, Kelly J, J. Collins K and Fergus S. Fas ligand expression in primary colon adenocarcinomas: evidence that the Fas counterattack is a prevalent mechanism of immune evasion in human colon cancer. J Pathol 1998; 186:240-246

O'Connell J, Houston A, Bennett M W, O'Sullivan G C and Shanahan F. Immune privilege or inflammation? Insights into the Fas ligand enigma. Nature Med. 2001; 7:271-274 (Commentary)

Patil Y and Panyam J. Polymeric nanoparticles for siRNA delivery and gene silencing. Int J Pharm 2009; 367:195-203

Rabinovitch M. Professional and non professional phagocytes: an introduction. Trends in cell biology 1995; 5:85-87

Ryan A E, Shanahan F, O'Connell J and Houston A M. Addressing the "Fas counterattack" controversy: blocking fas ligand expression suppresses tumor immune evasion of colon cancer in vivo. Cancer Res. 2005; 65:9817-9823

Sawyer T K. AILERON therapeutics. Chem Biol Drug Des (R&D Spotlight) 2009; 73:3-6

Sinha V R, Bansal K, Kaushik R, Kumria R and Trehan A. Poly-ε-caprolactone microspheres and nanospheres: an overview. Int J Pharm 2004; 278:1-23

Sukhorukov G B, Rogach A L, Garstka M, Springer S, Parak W J, Muç oz-Javier A, Kreft O, Skirtach A G, Susha A S, Racane Y, Palankar R and Winterhalter M. Multifunctionalized polymer microcapsules: Novel tools for biological and pharmacological applications. Small 2007; 3:944-955

Watanabe-Fukunaga et al., The cDNA structure, expression, and chromosomal assignment of the mouse Fas antigen. Journal of Immunology 1992; 148: 1274-1279

Walter E, Dreher D, Kok M, Thiele L, Kiama S G, Gehr P and Merkle H P. Hydrophilic poly(DL-lactide-co-glycolide) microspheres for the delivery of DNA to human-derived macrophages and dendritic cells. J Control Release 2001; 76:149-168

Weller M, Schuster M, Pietsch T, and Schabet M. CD95 ligand-induced apoptosis of human medulloblastoma cells. Cancer Lett 1998; 128:121-126

Zuliani C, Kleber S, Klussmann S, Wenger T, Kenzelmann M, Schreglmann N, Martinez A, del Rio J A, Soriano E, Vodrazka P, Kuner R, Groene H-J, Herr I, Krammer P H and Martin-Villalba A. Cell Death Diff. 2006; 13:31-40

The invention claimed is:

1. A composition comprising:
a polylactic-co-glycolic acid microparticle,
a chimeric fusion protein comprising a Fas protein or an extracellular domain of a Fas protein fused to a fragment crystallisable region (Fc region) of an immunoglobulin, said chimeric fusion protein being coupled to the surface of the microparticle via the immunoglobulin Fc region, and
a pharmaceutically active agent or marker, said agent or marker being contained in the polylactic-co-glycolic acid microparticle.

2. A composition as claimed in claim 1, wherein the chimeric fusion protein is human or murine.

3. A composition as claimed in claim 1, wherein the pharmaceutically active agent or marker not capable of specific binding to a Fas Ligand.

4. A composition as claimed in claim 1, wherein the chimeric fusion protein is coupled to the surface of the polylactic-co-glycolic acid microparticle by adsorption.

5. A composition as claimed in claim 1 further comprising one or more of a physiologically or pharmaceutically acceptable carrier, excipient, or stabilizer.

* * * * *